(12) United States Patent
Molnar et al.

(10) Patent No.: US 11,318,311 B2
(45) Date of Patent: May 3, 2022

(54) DEEP BRAIN STIMULATION SYSTEM AND METHOD WITH MULTI-MODAL, MULTI-SYMPTOM NEUROMODULATION

(71) Applicant: REGENTS OF THE UNIVERSITY OF MINNESOTA, St. Paul, MN (US)

(72) Inventors: Gregory Frederick Molnar, St. Paul, MN (US); Luke Johnson, St. Paul, MN (US); David Escobar Sanabria, St. Paul, MN (US); Edward Mark Bello, II, St. Paul, MN (US); Jerrold L. Vitek, St. Paul, MN (US); Matthew D. Johnson, St. Paul, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 0 days.

(21) Appl. No.: 17/002,136

(22) Filed: Aug. 25, 2020

(65) Prior Publication Data
US 2021/0038897 A1    Feb. 11, 2021

Related U.S. Application Data

(63) Continuation of application No. 15/788,563, filed on Oct. 19, 2017, now Pat. No. 10,786,676.
(Continued)

(51) Int. Cl.
*A61N 1/36* (2006.01)
*A61B 5/00* (2006.01)
(Continued)

(52) U.S. Cl.
CPC .......... *A61N 1/36139* (2013.01); *A61B 5/389* (2021.01); *A61B 5/398* (2021.01); *A61B 5/4064* (2013.01); *A61B 5/4806* (2013.01); *A61B 5/4812* (2013.01); *A61B 5/4836* (2013.01); *A61B 5/6868* (2013.01); *A61N 1/0534* (2013.01); *A61N 1/36067* (2013.01); *A61N 1/36078* (2013.01); *A61N 1/37258* (2013.01);
(Continued)

(58) Field of Classification Search
CPC .............. A61N 1/3603; A61N 1/36031; A61N 1/36078
See application file for complete search history.

(56) References Cited

U.S. PATENT DOCUMENTS

| | | |
|---|---|---|
| 2005/0177192 A1 | 8/2005 | Rezai et al. |
| 2009/0192556 A1 | 7/2009 | Wu et al. |
| 2017/0304587 A1 | 10/2017 | Santostasi et al. |

OTHER PUBLICATIONS

Abdullah, H. et al. "Phase Amplitude Coupling of Theta-Gamma EEG Frequency Bands in Sleep Apnoea". 2015 International Conference on BioSignal Analysis, Processing and Systems (ICBAPS). May 2015. pp 140-144. (Year: 2015).
(Continued)

*Primary Examiner* — Allen Porter
(74) *Attorney, Agent, or Firm* — Quarles & Brady LLP

(57) ABSTRACT

Described here is a deep brain stimulation ("DBS") approach that targets several relevant nodes within brain circuitry, while monitoring multiple symptoms for efficacy. This approach to multi-symptom monitoring and stimulation therapy may be used as an extra stimulation setting in extant DBS devices, particularly those equipped for both stimulation and sensing. The therapeutic efficacy of DBS devices is extended by optimizing them for multiple symptoms (such as sleep disturbance in addition to movement disorders), thus increasing quality of life for patients.

32 Claims, 11 Drawing Sheets

Related U.S. Application Data

(60) Provisional application No. 62/411,266, filed on Oct. 21, 2016.

(51) Int. Cl.

| | | |
|---|---|---|
| *A61N 1/372* | (2006.01) | |
| *A61N 1/05* | (2006.01) | |
| *G16H 50/20* | (2018.01) | |
| *G16H 20/30* | (2018.01) | |
| *G16H 40/63* | (2018.01) | |
| *A61B 5/389* | (2021.01) | |
| *A61B 5/398* | (2021.01) | |
| *A61N 7/00* | (2006.01) | |
| *A61N 2/00* | (2006.01) | |
| *A61N 1/20* | (2006.01) | |
| *A61N 1/378* | (2006.01) | |
| *A61B 5/291* | (2021.01) | |

(52) U.S. Cl.
CPC ............ *G16H 20/30* (2018.01); *G16H 40/63* (2018.01); *G16H 50/20* (2018.01); *A61B 5/291* (2021.01); *A61B 5/4082* (2013.01); *A61B 2503/40* (2013.01); *A61B 2503/42* (2013.01); *A61N 1/20* (2013.01); *A61N 1/3787* (2013.01); *A61N 1/37264* (2013.01); *A61N 2/006* (2013.01); *A61N 7/00* (2013.01); *A61N 2007/0026* (2013.01)

(56) References Cited

OTHER PUBLICATIONS

Amara, et al., Effects of Subthalamic Nucleus Deep Brain Stimulation on Objective Sleep Outcomes in Parkinson's Disease, Movement Disorders Clinical Practice, 2017, 4(2):183-190.

Amara, The Effect of Low Frequency STN DBS on Sleep and Vigilance in PD Patients, Project No. 4K23NS080912-05, Project Information—NIH Reporter, NIH Research Portfolio Online Reporting Tools, https://projectreporter.nih.gov/pr_Prj_info_desc_dtls.cfm. . . , Project Start Date: Sep. 26, 2012.

Arnulf, et al., Effect of Low and High Frequency Thalamic Stimulation on Sleep in Patients with Parkinson's Disease and Essential Tremor, Journal of Sleep Research, 2000, 9:55-62.

Barraud, et al., Sleep Disorders in Parkinson's Disease: The Contribution of the MPTP Non-Human Primate Model, Experimental Neurology, 2009, 219(2):574-582.

Belaid, et al., Sleep Disorders in Parkinsonian Macaques: Effects of L-Dopa Treatment and Pedunculopontine Nucleus Lesion, Journal of Neuroscience, 2014, 34(27):9124-9133.

Chouinard, Issues in the Clinical Use of Benzodiazepines: Potency, Withdrawal and Rebound, Journal of Clinical Psychiatry, 2004, 65(Suppl 5):7-12.

Daley, et al., Prolonged Assessment of Sleep and Daytime Sleepiness in Unrestrained Macaca Mulatta, SLEEP, 2006, 29(2):221-231.

Hess Jr., et al., Cortical and Subcortical Recordings in Natural and Artificially Induced Sleep in Cats, Electroencephalography and Clinical Neurophysiology, 1953, 5(1):75-90.

IBISWorld, Rest Easy: Growing Awareness and Coverage of Disorders Will Support Demand for Clinics, IBISWorld Industry Report OD5312, Sleep Disorder Clinics, Jun. 2015, 33 pages.

Kalorama Information, The World Market for Neurostimulation Devices (TENS, Carotid Sinus Nerve, Cochlear Implant, Deep Brain, Gastric Electrical, Phrenic Nerve, Sacral Nerve, Spinal Cord, Vagus Nerve, TMS, TNS and Other Stimulation Devices), Kalorama Information, Oct. 30, 2014, KLI5381556.

Kowal, et al., The Current and Projected Economic Burden of Parkinson's Disease in the United States, Movement Disorders, 2013, 28(3):311-318.

Li, D. et al. "Phase-Amplitude Coupling in Human Scalp EEG During NREM Sleep." 2015 8th International Conference on Biomedical Engineering and Informatics (BMEI). Oct. 2015. pp. 219-223 (Year: 2015).

Menza, et al., Sleep Disturbances in Parkinson's Disease, Movement Disorders, 2010, 25(Suppl 1):S117-S122.

Montine, Conference and Recommendations Report to the National Advisory Neurological Disorders and Stroke Council, Jan. 30, 2014, 31 pages.

Parkinson's UK, Q&A: Sleep and Night-Time Problems in Parkinson's, 2010, https://www.parkinsons.org.uk/content/qa-sleep-and-night-time-problems-parkinsons, 14 pages.

Partinen, Sleep Disorder Related to Parkinson's Disease, Journal of Neurology, 1997, 244(Suppl 1):S3-S6.

Qiu, et al., Deep Brain Stimulation in the Globus Pallidus Externa Promotes Sleep, Neuroscience, 2016, 322:115-120.

Salih, F. et al. "Functional Connectivity between Motor Cortex and Globus Pallidus in Human Non-REM Sleep". J. Physiol 587.5 ( 2009) pp. 1071-1086 (Year: 2009).

Sanabria, et al., Parkinsonism and Vigilance: Alteration in Neural Oscillatory Activity and Phase-Amplitude Coupling in the Basal Ganglia and Motor Cortex, Journal of Neurophysiology, 2017, 118:2654-2669.

Sanders, T. et al. "Sleep Stage Classification with Cross Frequency Coupling". 2014 36th Annual International Conference of the IEEE Engineering in Medicine and Biology Society. Aug. 2014. pp. 4579-4582 (Year: 2014).

Thompson, et al., Sleep Patterns in Parkinson's Disease: Direct Recordings from the Subthalamic Nucleus, Journal of Neurology Neurosurgery Psychiatry, 2017, 0:1-11, doi:10.1136/jnnp-2017-316115.

Timmermann, et al., Ten-Hertz Stimulation of Subthalamic Nucleus Deteriorates Motor Symptoms in Parkinson's Disease, Movement Disorders, 2004, 19(11):1328-1333.

Tsanas, et al., Stage-Independent, Single Lead EEG Sleep Spindle Detection Using the Continuous Wavelet Transform and Local Weighted Smoothing, Frontiers in Human Neuroscience, 2015, vol. 9, Article 181, 15 pages.

Videnovic, et al., Circadian and Sleep Disorders in Parkinson's Disease, Experimental Neurology, 2013, 243:45-56.

Ylikoski, et al., Sleeping Difficulties and Health-Related Quality of Life in Parkinson's Disease, Acta Neurol Scand, 2017, 135(4):459-468.

DEEP BRAIN STIMULATION SYSTEM AND METHOD WITH MULTI-MODAL, MULTI-SYMPTOM NEUROMODULATION

CROSS-REFERENCE TO RELATED APPLICATIONS

This application claims the benefit of U.S. Provisional Patent Application Ser. No. 62/411,266 filed on Oct. 21, 2016, and entitled "Deep Brain Stimulation System and Method with Multi-Modal, Multi-Symptom Neuromodulation," which is incorporated herein by reference in its entirety.

FEDERAL FUNDING STATEMENT

This invention was made with government support under grant nos. NS098573, NS037019, and NS081118 awarded by the National Institutes of Health and under grant no. DGE-1069104 awarded by the National Science Foundation. The government has certain rights in the invention.

BACKGROUND OF THE INVENTION

Deep brain stimulation ("DBS") has proven to be an effective treatment option for the motor symptoms of individuals with Parkinson's disease (PD). DBS has been used, for example, to treat medically intractable motor symptoms like tremor, slowness of movement, and rigidity in PD patients. But almost every patient with PD also suffers from some form of burdensome sleep disorder in addition to their motor and non-motor symptoms (e.g., autonomic, cognitive, mood, pain, etc.), and in many cases such sleep disorders and other symptoms of PD are not being effectively treated. DBS therapy is used to treat the motor symptoms of PD that manifest during the patient's awake-state, but no stimulation has been designed to treat sleep disturbances, which are common non-motor symptoms.

PD patients particularly suffer from the lack of complementary DBS therapy tailored towards their sleep-related comorbidities. Hitherto overlooked in therapeutic DBS design, sleep disturbances have a substantial impact on quality of life for this population. Sleep fragmentation, reduced total sleep time and efficiency, and rapid eye movement sleep behavior disorder (RBD), in conjunction with excessive daytime sleepiness, are reported in 74% to 98% of patients with PD. It is likely that all PD patients experience some sleep disturbances, albeit to varying degrees of severity, and this distressing comorbidity of PD has not yet been widely treated using DBS. These symptoms can be even more disabling and resistant to treatment than the motor symptoms of PD in some individuals. The number of people with PD is estimated at 1 million in the United States, 1.2 million in Europe, and 10 million worldwide, and these numbers are expected to double by mid-21st century. Due to the impact on quality of life and scarcity of effective therapeutic interventions, the National Institutes of Health-NINDS has identified the non-motor symptoms of PD, such as sleep, as an area of highest priority.

The current standard of care for patients with sleep disorders revolves around pharmaceutical interventions that vary in efficacy and reliability across patients and often come with undesirable side-effects. Drug treatments may include antidepressants, benzodiazepine sedatives, non-benzodiazepine hypnotics, antihistamines for insomnia, and stimulants for excessive daytime sleepiness. These medications are helpful for some patients in improving their sleep disturbances but are unfortunately also associated with significant adverse side effects and risks, such as cognitive impairment, dependence, and abuse. They also have high inter-subject variability in their effectiveness, resulting in inconsistent results among different patients suffering from different sleep disturbances. For example, the common medication for REM sleep behavior disorder (RBD) is clonazepam (a benzodiazepine), which can have persistent daytime effects that result in sedation, cognitive impairment, and falls. Moreover, sleep medication efficacy is complicated by medication regimens that are administrated to treat other symptoms. For example, dopaminergic medications given to treat motor symptoms of patients with PD can themselves cause sleep issues like insomnia and daytime sleep attacks.

SUMMARY OF THE INVENTION

What are needed are more effective and less adverse treatments for sleep disturbances and other disorders. A DBS-based solution would be applicable in the subset of patients who already receive this therapy to reduce motor symptoms of PD, but it need not be limited to this population. As an example, those that suffer severe treatment-resistant sleep disorders certainly stand to benefit from DBS tailored towards sleep improvement.

Sleep disorders are associated with a decline in quality of life in people of all ages, including children, adults, and seniors. The disclosed invention, in exemplary embodiments, involves DBS sensing and stimulation techniques that provide detection of sleep stages and relief from sleep disturbances, with the ability to continue providing effective therapy for other symptoms being treated using a DBS system, such as motor symptoms in PD patients. Exemplary DBS systems are controlled so as to deliver diagnostics by tracking patient sleep architecture, as well as therapeutics by delivering optimal stimulation parameters at relevant sleep stages to improve overall sleep quality. Modulating sleep to treat sleep disorders via DBS would benefit not only PD patients, but others as well in the general population, such as persons with intractable, treatment-resistant sleep disorders. Advantageously, a reduction in the need for medications and associated side effects would be expected to increase a patient's quality of life and productivity, and could reduce healthcare costs.

In some exemplary embodiments, the invention may be implemented using existing DBS systems by enhancing/augmenting control mechanisms so as to target sleep disorders (via, for example, firmware updates). Implementing augmented control mechanisms in existing DBS systems can provide already-implanted patients with easy access to expanded therapies without the risks associated with additional surgical procedures. For example, sleep disturbances in the population of PD patients implanted with DBS systems may be more effectively diagnosed and treated by detecting and modulating sleep waves via the same deep brain leads that are currently implanted to treat motor symptoms. This multi-objective approach to therapy (e.g., treating motor and sleep symptoms with the same implant) is a paradigm shift that will be preferred by patients, clinicians, and the health system because only one intervention is needed to address two or more symptoms.

This disclosure provides a novel approach to deep-brain stimulation (DBS) therapy for managing multiple symptoms simultaneously through multi-modal, targeted strategies that enable the treatment of various neurological conditions and co-morbid conditions. Conditions treated by neuromodulation therapies—such as pain, movement disorders, and psychiatric disorders—often have multiple symptoms. When a specific brain target and therapy are used to treat one symptom, discomfort or other symptoms may arise. Additionally, many neurological disorders carry with them comorbidities that may be ameliorated by DBS.

For example, PD has both motor symptoms such as rigidity and non-motor symptoms such as sleep disturbances. Currently, the motor symptoms are treated with DBS in the subthalamic nucleus (STN), globus pallidus (GP), and thalamus. The stages and quality of sleep can be detected by electrophysiological recordings in the same brain regions that are administered DBS to treat motor symptoms. In stimulating these brain regions, the waveforms and patterns/frequencies delivered to these same targets can be used to promote/enhance sleep.

Thus, certain embodiments of this invention augment DBS therapy to treat both the motor and non-motor symptoms of PD by incorporating novel algorithms to detect, monitor, and improve sleep quality. These algorithms will incorporate circuit specific therapy signals at the appropriate times, as will be further discussed below (see, e.g., FIG. 3), to promote sleep. One can detect sleep from deep brain structures, while stimulating therein (see, e.g., FIG. 4). This multi modal and multi-symptom therapy can employ, in other embodiments, novel electrodes/leads to span multiple brain targets and multiple sensors or wearables to best inform the DBS system of the patient's clinical state. Multiple and simultaneous waveforms can be used to target specific brain circuits which cause specific symptoms. Various stimulation modalities may be used to accomplish therapeutic neuromodulation (i.e. electrical, magnetic, optical, sound/ultrasound, etc.) or targeted drug delivery therapies. For example, the sensors may trigger an electrical modulation response or communicate and trigger the flow of drug via an implanted drug pump, or trigger an alert on the patient's device programmer to take their scheduled or PRN (i.e., on an "as needed" basis) oral medications. Similarly, the deep brain leads may modulate via optogenetic stimulation in conjunction with triggering external ultrasound or magnetics stimulators for a combined effect.

The invention thus provides, in various embodiments, a novel method of spanning multiple brain targets for multiple symptoms, which may be employed at different times depending on the clinical symptoms and clinically relevant states, such as sleep versus awake states. In particular, the use of novel DBS waveforms and stimulation parameters is useful for inducing a sleep state in subjects with sleep disturbances as a comorbidity, as well as subjects with idiopathic sleep disorders.

A multi-modal stimulation coupled with multi-symptom feedback can offer an effective approach to treat both the primary symptoms of a DBS-ameliorable disease, along with any DBS-ameliorable comorbidities. Not only are such natural comorbidities treated, but DBS-induced side-effects are controlled and counteracted by monitoring them in real time. Different parameters of stimulation can be delivered to the same targets stimulated during the day to promote quality sleep; electrophysiological biomarkers for the sleep state can be monitored to adjust stimulation accordingly.

DBS is often used to counteract the motor symptoms of a diagnosed disease, but has not seen widespread use in treating multiple brain targets for multiple major symptoms. In the case of PD-related sleep disorders, the use of pharmacological interventions may be minimized by utilizing the already-implanted DBS hardware and delivering sleep-improving stimulation when needed.

In accordance with one aspect of the present disclosure, a method is provided for treating a sleep disorder using deep brain stimulation (DBS). The method includes steps of: receiving and processing readings from a neurosensor implanted in the brain of a subject to evaluate a current neural state of a subject, the neurosensor being connected to an implantable pulse generator (IPG); and based on the current neural state, stimulating the brain of the subject via a neurostimulator to induce a modified sleep state, the neurostimulator being connected to the IPG.

In accordance with another aspect of the present disclosure, a method is provided for treating two or more symptoms of a subject using deep brain stimulation (DBS). The method includes steps of: receiving and processing readings from a neurosensor implanted in the brain of a subject to evaluate a current neural state of a subject, the neurosensor being connected to an implantable pulse generator (IPG); and based on the current neural state, stimulating the subject's brain via a neurostimulator to induce a modified neural state, the neurostimulator being part connected to the IPG.

In accordance with still another aspect of the present disclosure, a system is provided for treating a sleep disorder using deep brain stimulation (DBS). The system includes: a lead including a set of electrodes for taking readings from, and stimulating, one or more regions of a subject's brain; and an implantable pulse generator (IPG) including a neurostimulator and a neurosensor for using the set of electrodes to both stimulate neurons and obtain readings from the subject's brain. The IPG in turn includes a controller configured to receive and process electrical data from the subject's brain via the neurosensor to detect a current neural state of the subject; and based on the current neural state, stimulate the subject's brain via the neurostimulator to induce a modified sleep state.

In accordance with yet another aspect of the present disclosure, a deep brain stimulation (DBS) system is provided for treating a sleep disorder using deep brain stimulation. The system includes a controller including a processor and instructions that, when executed by the processor, configure the DBS system to: receive and process readings from a neurosensor to evaluate a current neural state of a subject, the neurosensor being implanted in a brain of a subject and connected to an implantable pulse generator (IPG); and based on the current neural state, stimulate the brain of the subject via a neurostimulator to induce a modified sleep state, the neurostimulator being connected to the IPG.

In accordance with yet another aspect of the present disclosure, a method is provided for controlling a deep brain stimulator (DBS) implanted in a brain of a subject. The method includes the steps of: receiving electrical data obtained from a sub cortical structure of the brain of the subject; determining a sleep stage of the subject based on analyzing the electrical data; and adjusting control of the DBS based on determining the sleep stage of the subject.

In accordance with still another aspect of the present disclosure, a method is provided for modulating sleep in a subject. The method includes the steps of: stimulating a sub cortical structure of a brain of the subject using a deep brain stimulator (DBS) implanted in the brain of the subject to alter a sleep stage of the subject, stimulating comprising applying a patterned stimulation to the sub cortical structure using the DBS.

In accordance with yet another aspect of the present disclosure, a deep brain stimulation (DBS) system is provided. The DBS system includes: a controller including a processor and instructions that, when executed by the processor, configure the DBS system to: receive electrical data obtained from a subcortical structure of a brain of a subject; determine that the subject is in a REM sleep stage or an NREM sleep stage based on analyzing the electrical data; and adjust therapeutic stimulation of the DBS based on determining that the subject is in the REM sleep stage or the NREM sleep stage.

In accordance with still another aspect of the present disclosure, a deep brain stimulation (DBS) system is provided. The DBS system includes: a controller including a processor and instructions that, when executed by the processor, configure the DBS system to: stimulate a subcortical structure of a brain of a subject to alter a sleep stage of the subject, stimulating comprising applying a patterned stimulation to the subcortical structure.

The foregoing and other aspects and advantages of the invention will appear from the following description. In the description, reference is made to the accompanying drawings which form a part hereof, and in which there is shown by way of illustration preferred embodiments of the invention. Such embodiments do not necessarily represent the full scope of the invention, however, and reference is made therefore to the claims herein for interpreting the scope of the invention.

DETAILED DESCRIPTION OF THE INVENTION

Figure 1A:
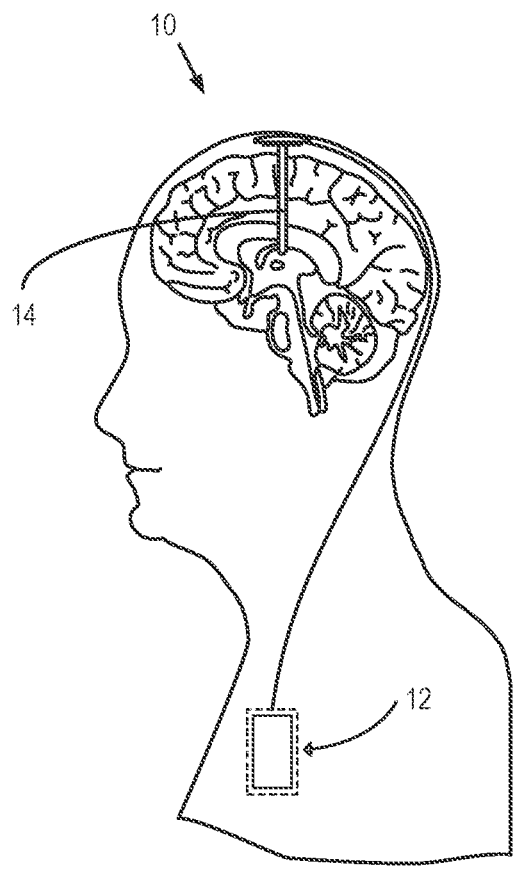
FIGS. 1A and 1B show an exemplary deep brain stimulation ("DBS") system connected to an implantable pulse generator (IPG), where the DBS system includes one or more leads implanted in the brain of a subject.
Figure 1B:
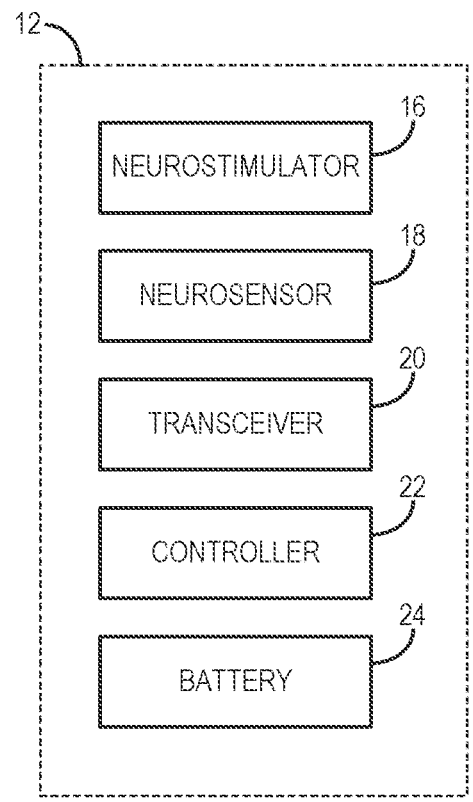
Figure 2:
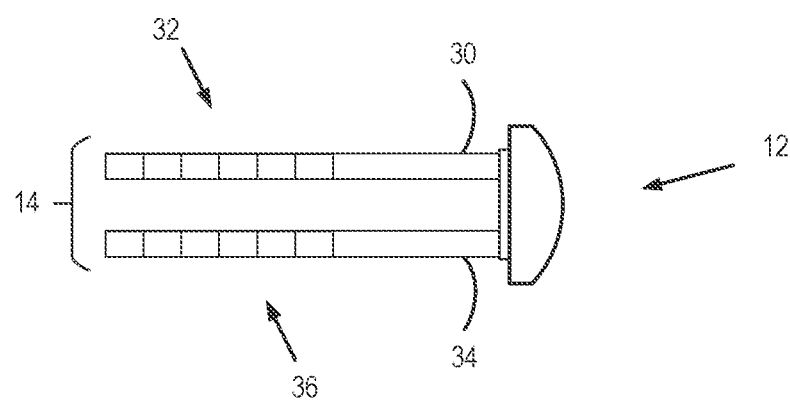
FIG. 2 is a close-up view of the leads of the DBS system of FIGS. 1A and 1B, showing that each lead includes a set of electrodes, and depicting an alternative embodiment in which the IPG is integrated into the portion of the DBS that is implanted in the brain.

Described here is a deep brain stimulation ("DBS") system and method that uses electric potentials or/and electromagnetic fields for the diagnosis, monitoring, and treatment of sleep-related disorders. An example of such a DBS system is represented in FIGS. 1A and 1B. The DBS system 10 includes an implantable pulse generator (IPG) 12 that is electrically connected to one or more leads 14 implanted in the brain of a subject. In various embodiments the subject may be a human, a non-human primate (NHP), or another animal. In certain embodiments (e.g. FIG. 1A), the IPG 12 contained in a separate housing that may be implanted in the thoracic region of the subject and connected to the portion of the DBS system 10 (e.g. which includes the leads 14) that is implanted in the brain, for example by a cable as shown in FIG. 1A. In other embodiments, the IPG 12 may be integrated into the implanted portion of the DBS, for example as indicated in FIG. 2.

The IPG 12 includes a neurostimulator 16 for sending electrical pulses into the brain to generate electric currents that stimulate neurons (and thus influence neural activity at a target site), and a neurosensor 18 for reading electrical signals from a target site in the brain. A transceiver 20 (which may use, e.g., Bluetooth or other wireless communications technology) can be included to allow data (such as sensed signals) to be transmitted to another system, and/or to allow data (such as commands and stimulation patters) to be received. A controller 22, which can be accessed using, e.g., a remote control via transceiver 20, includes a processor and memory for storing instructions (to be executed by the processor) for processing data (such as sensed brain activity), initiating stimulation, etc. Battery 24, which may be inductively rechargeable, is used as a source of energy for the IPG 12. Referring to FIG. 2, the one or more leads 14 of IPG 12 may include a first lead 30 having a first set of electrodes 32, and a second lead 34 having a second set of electrodes 36. Each electrode can be independently driven using stimulation signals generated by the neurostimulator 16 under control of the controller 22, which may additionally include a digital-to-analog converter.

In exemplary embodiments, the DBS system enables the assessment of sleep architecture and quality (i.e., NREM and REM sleep) through the implanted DBS device without the need for typical polysomnography recordings in a sleep clinic or hospital. This would allow sleep specialists to assess the patient's sleep over time and inform treatment choices. Additionally, the DBS system modulates brain activity to restore a patient's normal sleep architecture by addressing issues with particular sleep stages. This may be accomplished, for example, by inducing and/or extending slow wave sleep and/or altering stimulation during REM sleep to disrupt the abnormal muscle activation that occurs during REM sleep behavior disorder (RBD).

Figure 3:
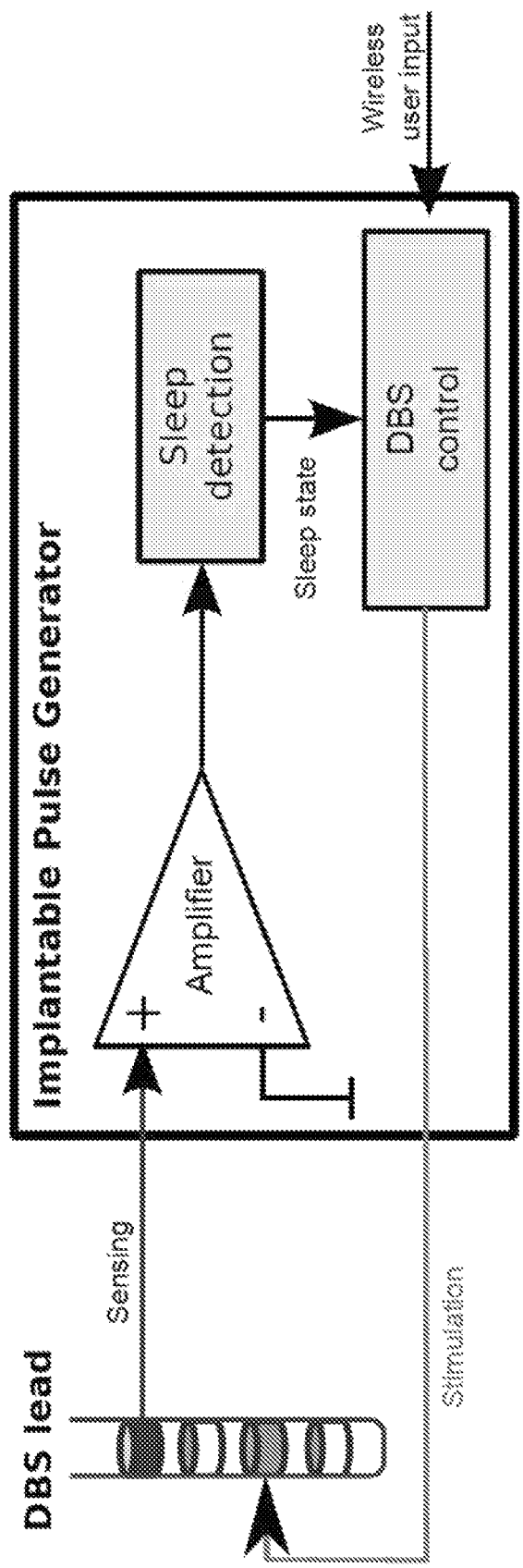
FIG. 3 is a functional schematic of an exemplary DBS system to be used to treat sleep disturbances in, e.g., patients with Parkinson's disease (PD). The system is capable of sleep detection and DBS control to simultaneously alleviate sleep disturbances and motor systems.

Referring to FIG. 3, an exemplary DBS system includes at least one DBS lead with one or more electrodes used for sensing, and one or more electrodes used for stimulation. Signals sensed using the electrical lead of the DBS system may be relatively faint, and can thus be amplified using an amplifier (which may be part of the neurosensor 16 in FIG. 1B) and analyzed for sleep detection. Analysis may occur separately (by, e.g., an external/separate computing system that receives readings from the IPG via the transceiver 20, such as a mobile device or a workstation), and/or by the IPG itself (using, e.g., controller 22). Identified sleep states can be provided by the external system to the DBS controller, which can process and initiate stimulation of a targeted region of the brain. The IPG is preferably able to receive user input (such as instructions on when or how to initiate stimulation) wirelessly using its transceiver.

Figure 4:
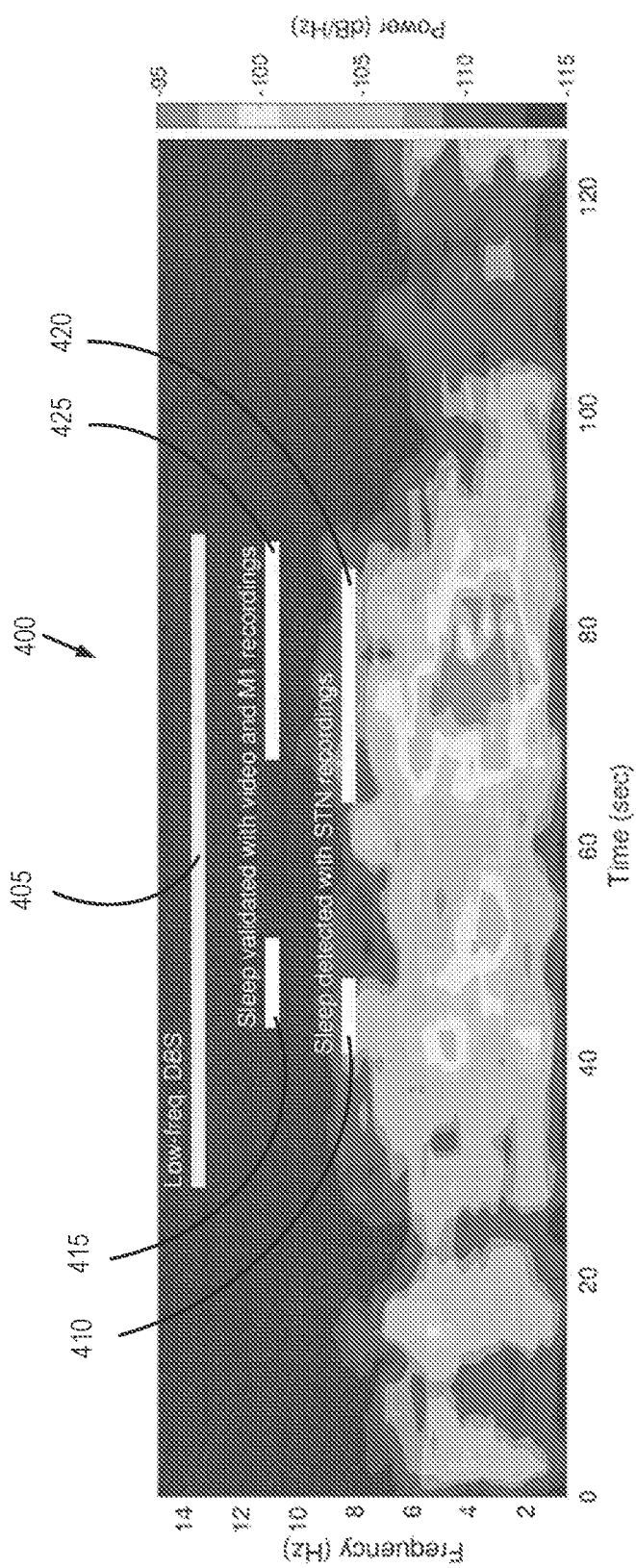
FIG. 4 is a time-frequency spectrogram of a unipolar subthalamic nucleus (STN) recording from a parkinsonian non-human primate ("NHP") before, during, and after a period of low-frequency (5 Hz) deep brain stimulation. This represents simultaneous sensing and stimulation through an STN-DBS electrode, and data show sleep can be identified through spectral analysis and detection algorithms based on recordings from another contact on the same DBS electrode array used for stimulation.

Preclinical experiments in normal and parkinsonian non-human primates ("NHP") have shown that the DBS system allows for the detection of early stages of sleep using DBS implants in subcortical structures while stimulating at low frequencies. FIG. 4 shows data from simultaneous sensing and stimulation via DBS electrodes in awake and sleep states. The time-frequency spectrogram (400) of a unipolar STN recording in FIG. 4 shows that a low-frequency stimulation (405) at 5 Hz was imposed for about a minute starting at about time 30 seconds. Periods of drowsiness and sleep followed, which can be identified using spectral analysis and detection based on recordings from another contact on the same DBS electrode array used for stimulation.

As can be seen in FIG. 4, sleep lasting for approximately 10 seconds (410) was identified based on electrode readings beginning at approximately time 40 seconds. This first sleep period corresponded with video recordings (i.e., eye camera videos) and field potential recordings from the M1 motor cortex (415), both of which provide validation for the detected sleep. Similarly, early non-REM sleep lasting for approximately 20 seconds (420) was identified based on electrode readings starting at approximately time 65 seconds. This second sleep period was also validated using video recordings and field potential recordings from the M1 motor cortex (425).

Readings that indicate sleep (and different stages thereof) can vary for different individuals, but is expected to be correlated with lower power levels at certain frequencies. For example, in spectrogram 400, sleep was observed with power levels ranging from −100 to −95 dB/Hz (which is lower than surrounding power levels that mostly fell in the range of −115 to −100 dB/Hz) at lower frequencies of 2 to 8 Hz. Sleep measurements can be used for device tuning, assessment of the efficacy of the DBS sleep therapy, and automatic adjustment of DBS parameters in different vigilance states. Different patterns of DBS may modulate oscillatory activity associated with non-REM and REM sleep stages. Based on observations in the laboratory with a non-human primate, low-frequency stimulation in the thalamus may promote drowsiness and sleep; this contrasts with standard DBS therapy, which delivers high-frequency stimulation.

Figure 5:
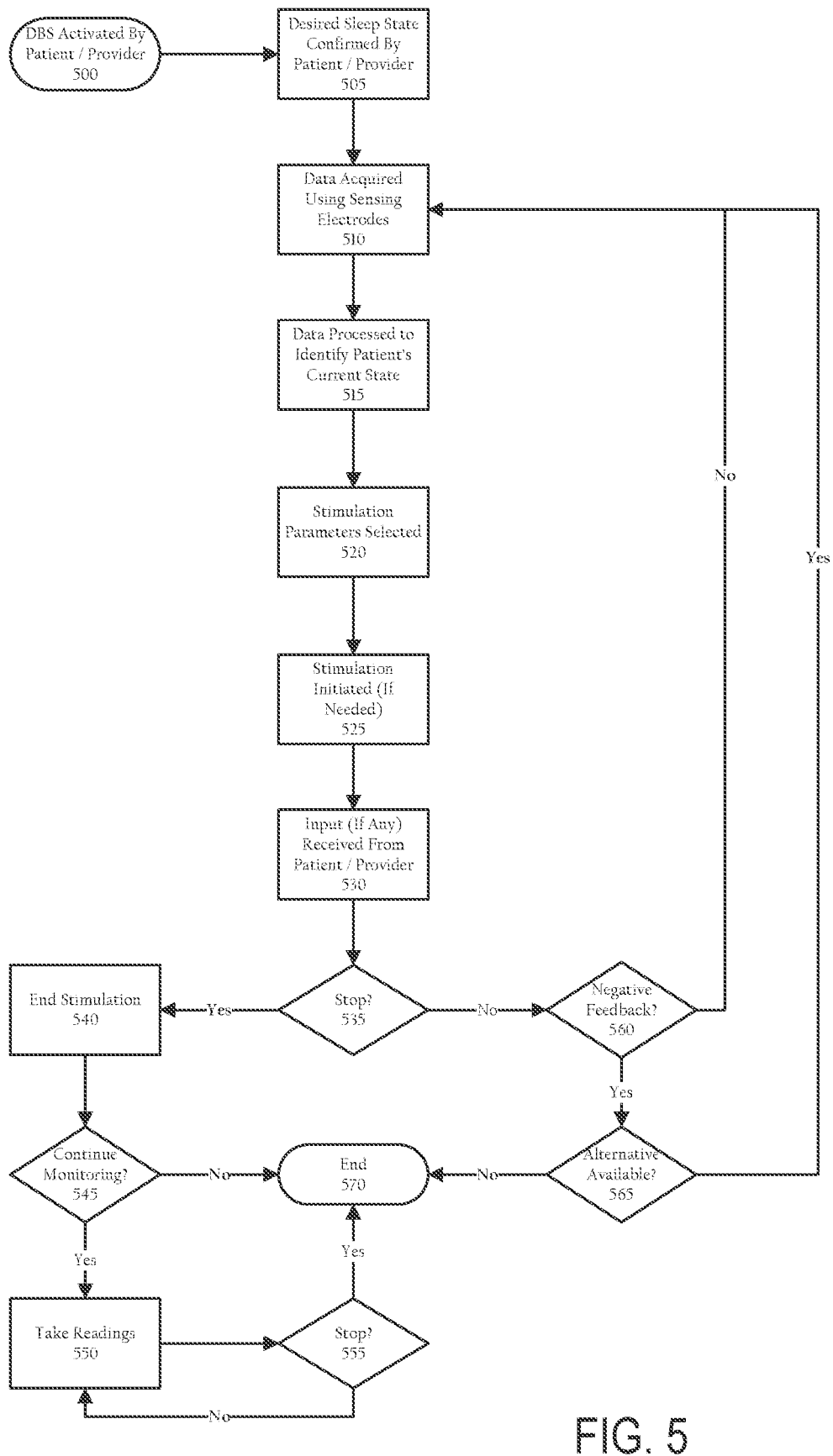
FIG. 5 provides a flowchart with an exemplary sequence of events according to various embodiments of the invention in which sleep disturbances are to be treated.
Figure 6:
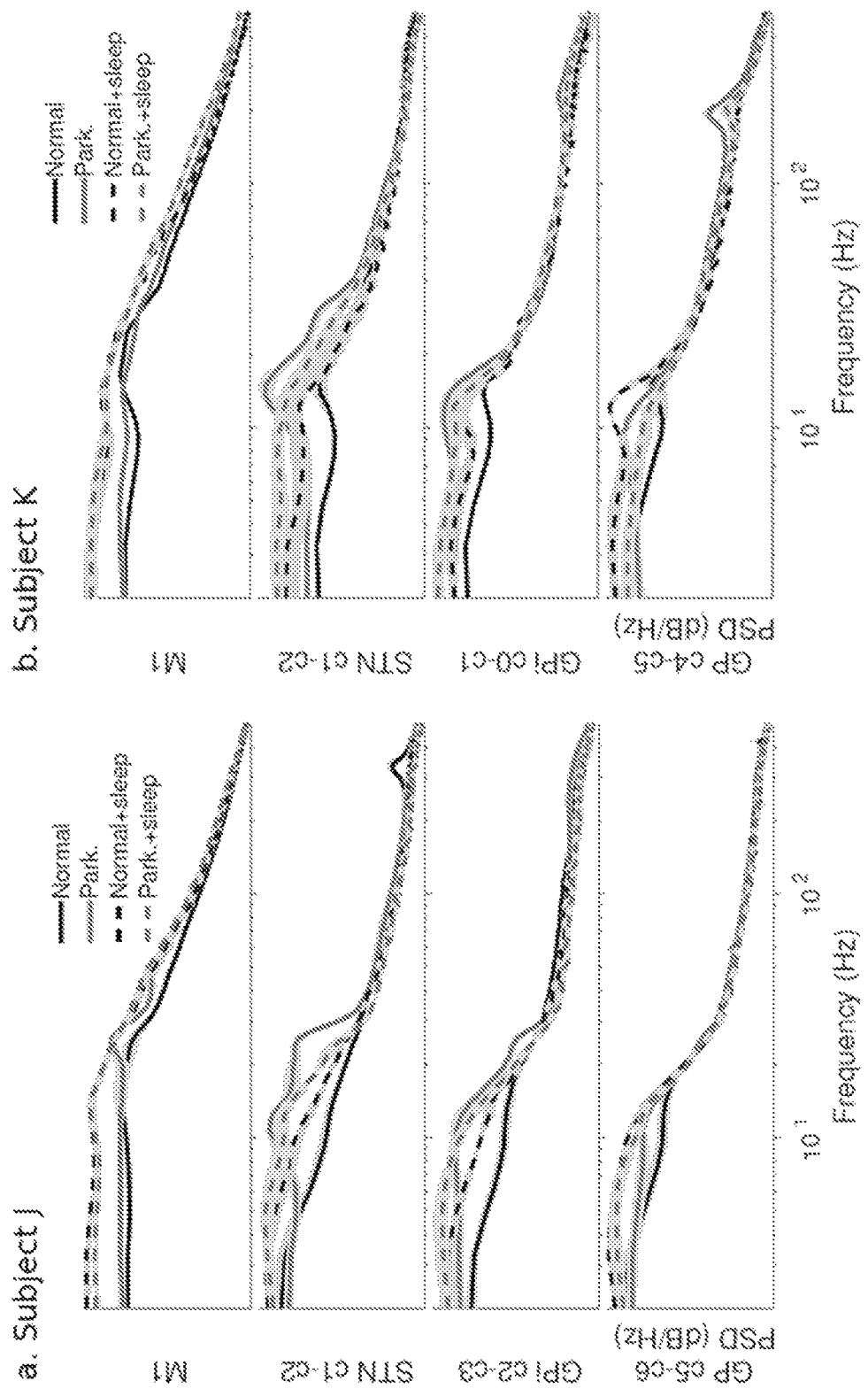
FIG. 6, related to oscillatory activity, provides power spectral densities (PSD) that reveal differences in oscillatory activity between awake and sleep states in two subjects. Recordings from the primary motor cortex (M1), subthalamic nucleus (STN), and internal and external segments of the globus pallidus (GPe/i) are shown. It is noted that the disease state causes a change in the structure of the PSD, but that in both the disease and healthy states, sleep alters that structure as well. In other words, whether normal or parkinsonian, sleep state can be detected based on characteristics of the oscillatory activity (e.g., amplitude of low frequency power and/or relative levels of high and low frequency power).

Referring to the exemplary flowchart in FIG. 5, the DBS system may first be activated by the patient or by the patient's healthcare provider (500). This may involve the patient using a remote control or external computing device to turn the DBS system on, or to otherwise initiate its sleep control protocols. A desired sleep state may be entered and/or confirmed by the patient/healthcare provider (505), if multiple sleep states are available. For example, the patient may wish to indicate that s/he intends to sleep for the entire night, and would thus like a corresponding amount of REM sleep. Alternatively, the patient may submit that a one-hour "nap" is desired, or that no sleep is desired, in which case the DBS system may be focused on monitoring brain activity (using sensing electrodes) without stimulating for inducing a sleep state. Such monitoring may be particularly useful for, e.g., calibrating the DBS system before initial use, to fine-tune the system during continued use, or to incorporate refined parameters based on data not already available from prior recordings from a particular patient.

The DBS system may then acquire data using sensing electrodes (510), and process that data to identify the patient's current neurological state (515). This may provide useful information in determining how best to modulate signals to achieve the desired sleep state. Based on the current state, and the patient's desired state, a set of parameters for stimulation can be selected (520) and stimulation initiated, if appropriate (525). If sleep is not to be induced, and only monitoring is to be conducted, then there may be no sleep-inducing stimulation initiated.

The DBS system may receive inputs from the patient (or healthcare provider) (530), who may have just experienced stimulation intended to promote sleep. If the patient has changed his/her mind, or decided that the effects are undesirable, the patient may indicate that s/he would like to stop the treatment (535). If so, the stimulation is ended (540), and it is determined (based on a prior entry by the patient/healthcare provider, or in response to a new query) whether monitoring of neurological activity should continue (545). If monitoring is to continue, the DBS system takes readings (550) for a set duration, until certain observations are made, or until instructed to stop by the patient/healthcare provider (555). If monitoring (545) is not to continue, or if readings are to stop (555), then the DBS system may end its sleep-related protocols (570).

If the patient/healthcare provider does not experience a desirable outcome (e.g., if the stimulation does not induce drowsiness but instead awakens the patient or brings about undue anxiety, or if stimulation has caused discomfort), the patient may provide "negative" feedback (560), by, e.g., identifying undesirable experiences. If there is no negative feedback, or if feedback is positive, the DBS system again acquires data using sensing electrodes (510) to identify the patient's current state (515), and either elects to continue with the same stimulation parameters as before (520), or modifies parameters based on the changes in the patient's current state (as determined from readings (510) or feedback (560)). If the patient provides negative feedback (560), the DBS system may determine whether a suitable alternative stimulation strategy is available (565), based on the patient's current state, desired outcome, past experiences, and/or data available from stimulation of patients with comparable neurological indicators.

If no alternative is available, the DBS system may end (570) the sleep promotion process. If a potential alternative stimulation strategy is known, the DBS system acquires (510) and processes (515) recorded data to better understand the patient's current state and determine which particular alternative/parameters (if any) are suitable to try (520). It is noted that if there is no intervention from the patient/healthcare provider (530)—i.e., if there is no "stop" command (535), and if the DBS system has not exhausted all its available strategies to no avail (565)—then the DBS system continues in a loop in which data is recorded (510), processed (515), and (potentially new or revised) stimulation parameters are selected (520) and applied (525).

In exemplary versions, the therapeutic being developed may be implemented as a software suite to be incorporated into DBS implant technology (e.g. Medtronic Activa RC+S) for PD. The software characterizes sleep architecture based on the physiological signals recorded from the implanted DBS leads and adjusts DBS parameters in order to address patient-specific sleep disorders. The ability to detect specific sleep stages will open the possibility of a targeted therapy that treats specific sleep disorders such as REM sleep behavior disorder, in which patients have abnormal muscle activation during the REM sleep stage and for which simulation may be optimized to restore atonia or minimize movement. For patients with insomnia (difficulty falling asleep and/or frequent awakenings), DBS stimulation may be optimized to promote and extend slow waves associated with non-REM sleep. This potential therapy was identified based on observations in NHP that sleep may be detected based on local field potential recordings from DBS implants in the subthalamic nucleus (STN) and external and/or internal segments of the globus pallidus (GPe/i). The high connectivity of basal ganglia nuclei and sleep circuits (e.g., via projections to and from the pedunculopontine nucleus and the thalamus) provides a basis for optimizing DBS settings to treat sleep disturbances in PD patients who receive DBS. As suggested above, the ability to incorporate these algorithms into existing DBS technologies without the need for new surgical interventions is a significant advantage.

During a routine deep-brain stimulation experiment in a NHP, it was observed that upon turning on low-frequency stimulation (traditional DBS is delivered at high frequencies, around 130 Hz), the NHP dozed into the first state of sleep. Upon turning off the low-frequency stimulation, the NHP came back into an alert state. This effect was repeated several times. In other experiments with animals that were implanted in the STN and GPi with scaled-down versions of human DBS leads, data was collected using the DBS leads (not just simply stimulating through the leads) while animals were in a passive resting condition. These experiments were focusing on awake rest recordings, and so it was not initially desired that animals fall asleep; nonetheless, animals occasionally spontaneously fell asleep. Sleep epochs were especially common after the animal became parkinsonian via administration of the neurotoxin MPTP. Marked changes in the neural activity patterns in these deep brain structures during sleep were discovered. These findings, combined with the findings that non-traditional stimulation frequencies may induce sleep, led to development of closed-loop algorithms for monitoring and modulating sleep.

The sleep detection and staging algorithms may employ two recording modes (monopolar and bipolar) to detect sleep stages and signatures of PD associated with their sleep disorder. Monopolar recordings (in which the reference electrode is distant, e.g. at the IPG housing, e.g. FIG. 1A) from individual contacts on the DBS array are used to capture long-range brain rhythms that are associated with particular sleep stages as they are traditionally defined (non-REM stage 1-4, REM, etc.). Bipolar potential recordings (e.g. reference electrode is a nearby contact on the DBS array) are used to measure short-range neuronal activity at high-frequency that is also associated with sleep (e.g. sleep spindles).

Information about sleep stages can be determined by evaluating low-frequency brain rhythms characteristic of sleep that exist in both healthy and parkinsonian subjects, as supported by evidence from non-human primate studies. Moreover, certain electrophysiological biomarkers characteristic of the disease state (e.g. phase amplitude coupling, PAC) that are prominent in the awake state but are altered in sleep state (e.g., reduced strength and/or change in phase of coupling) may be used to characterize sleep stages. For example, a strong PAC measured in the globus pallidus external segment in the awake parkinsonian animal (not present in the healthy animal) diminishes when the animal becomes drowsy and falls asleep. Throughout a full sleep cycle of neural activity, it is expected that PAC changes observed in early sleep stages would be different during REM sleep stage and may complement the spectral analysis techniques described below.

In order to promote sleep, sleep-specific stimulation through a DBS array may be activated at appropriate times (or stages of sleep), as suggested above. Stimulation patterns can include traditional static frequency stimulation, as well as variable frequency approaches. One such example would be a high-frequency to low-frequency "chirp" signal, which resembles the "slowing" of oscillations in the brain as a patient falls into deeper sleep-states. A variable transition of f0 to f1 can be attempted, the rate at which the frequency varies can be modulated, and effects on sleep observed. Burst stimulations can be tried, by varying the inter-burst frequency, intra-burst frequency, and the length of the burst epoch.

Preliminary data collected in NHPs has demonstrated similar sleep patterns as humans, and in the parkinsonian state, NHPs exhibit sleep disturbances and excessive daytime sleepiness similar to people with PD. The NHPs studied were adult female rhesus macaques (*Macaca mulatta*, aged 13 and 17). All surgery was performed using aseptic techniques under isoflurane anesthesia. Pre-operative cranial CT and 7-T MRI images were incorporated into the Monkey Cicerone neurosurgical navigation program to facilitate surgical planning of a titanium cephalic chamber targeting the STN, GPe and GPi. Extracellular microelectrode mapping confirmed the location of target nuclei. Each animal was then implanted in both the STN and GP with 8-contact scaled versions of human DBS leads (0.5 mm contact height, 0.5 mm inter-contact spacing, 0.625 mm diameter, NuMED, Inc.) using known methods. Each animal was subsequently implanted in the arm area of primary motor cortex (M1) with a 96-channel Utah microelectrode array (Pt—Ir, 1.5 mm depth, 400 um inter-electrode spacing, Blackrock Microsystems) using known surgical methods. Pt/Ir reference wires were placed between the dura and skull adjacent to the array. During array implantation surgery, M1 was identified based on sulcal landmarks, and the arm area was localized based on intra-operative stimulation of the cortical surface using a stainless steel ball electrode (Grass Technologies). The motor cortex recordings were used as a proxy for cortical EEG recordings and confirmation of sleep state along with eye opening and closing. Locations of DBS leads were verified in one NHP subject histologically using frozen coronal sections (50 um thick) that were imaged and visualized in Avizo 3D analysis software (FEI). DBS lead locations were verified using fused pre-implantation MRI and post-implantation CT images in the other NHP subject.

Once data were collected in the normal state, animals were rendered parkinsonian by systemic (intramuscular) and intra-carotid injections of the neurotoxin 1-methyl-4-phenyl-1,2,3,6 tetrahydropyridine (MPTP). One subject received six intramuscular injections (0.3-0.4 mg/kg each, total 0.19 mg/kg), while the other received three intramuscular and one intra-carotid injections (0.3-0.4 mg/kg each, total 0.13 mg/kg). For both subjects, data were gathered after a stable parkinsonian state was achieved, beginning approximately one month after the last MPTP injection and continuing for one to two months. Motor symptoms were assessed using a modified Unified Parkinson's Disease Rating Scale (mUPDRS) which rated axial motor symptoms (gait, posture, balance) as well as upper and lower limb rigidity, bradykinesia, akinesia and tremor on a 0-3 scale (0=normal, 3=severe, maximum total score of 18). One subject received daily dopaminergic treatment (carbidopa/levodopa 25/100 mg tablets) at the end of the day's experimental sessions to facilitate animal's care in its home enclosure; however, all neurophysiology recordings were conducted a minimum of 16 hours after the last treatment dose. Animals were in a moderate to severe parkinsonian state for axial symptoms and bradykinesia, rigidity, and akinesia.

Neurophysiological data were collected using a TDT workstation (Tucker Davis Technologies) operating at ~25 KHz sampling rate. Signals were bandpass filtered (0.5-700 Hz) and down-sampled to ~3 kHz for analysis. Monopolar LFPs from the STN and GP were recorded referenced to a ground screw on the animal's head. Bipolar LFPs were generated by subtracting recordings from adjacent contacts of the DBS leads (e.g. LFP C0-C1 represents the signal created by subtracting contact 1 from contact 0). A mean M1 LFP was obtained by averaging recordings from all 96 channels in the array and used for confirmation of sleep state along with eye open state. All data were collected during a resting state while the animal was seated in a primate chair with its head fixed. Time periods with movement artifacts were identified by high amplitude broadband power in the time-frequency spectrogram (spectral analysis described below) and excluded from further analysis.

Regarding sleep detection algorithm, sleep stages N1, N2, and N3 are traditionally classified via identification of K-complexes, slow waves, and delta oscillations (0.4-4 Hz) in electroencephalography recordings. It was observed that a proxy of these low-frequency signal features is the oscillatory activity recorded from monopolar potentials in basal ganglia nuclei (STN, GPi, GPe). To detect non-REM sleep (N1, N2, or N3 stages) particularly, the instantaneous power of the monopolar potential was used. A measure of the low-frequency power at each sample time k denoted by P(k) is computed by bandpass filtering (any filtering technique) the monopolar potential in the 0.1-7 Hz range, obtaining the amplitude envelope of the low-frequency oscillations via the Hilbert transform or by rectifying the signal, and smoothing the envelope via a low-pass filter of cutoff 0.2 Hz (using any filtering technique). A threshold Pt is used to classify, given the low-frequency power envelope, whether the subject is in the NREM-sleep or awake state. The threshold Pt is computed as follows. First, a prolonged period of time in which the subject is in the awake state with its eyes open was selected by inspecting video recordings. Then, the maximum value of the low-frequency power envelope during this period was selected as the threshold Pt. The expression below summarizes how at each sample k the vigilance state Sv(k) was estimated based on the low-frequency power in the basal ganglia nuclei.

$$Sv(k)=1 \text{ (awake) if } P(k)<Pt$$

0 (sleep) otherwise

The detection algorithm was validated by quantifying the instantaneous eye-opening of the subjects from video recordings and the low-frequency oscillations from recordings in the motor cortex (Utah electrode arrays).

Figure 7:
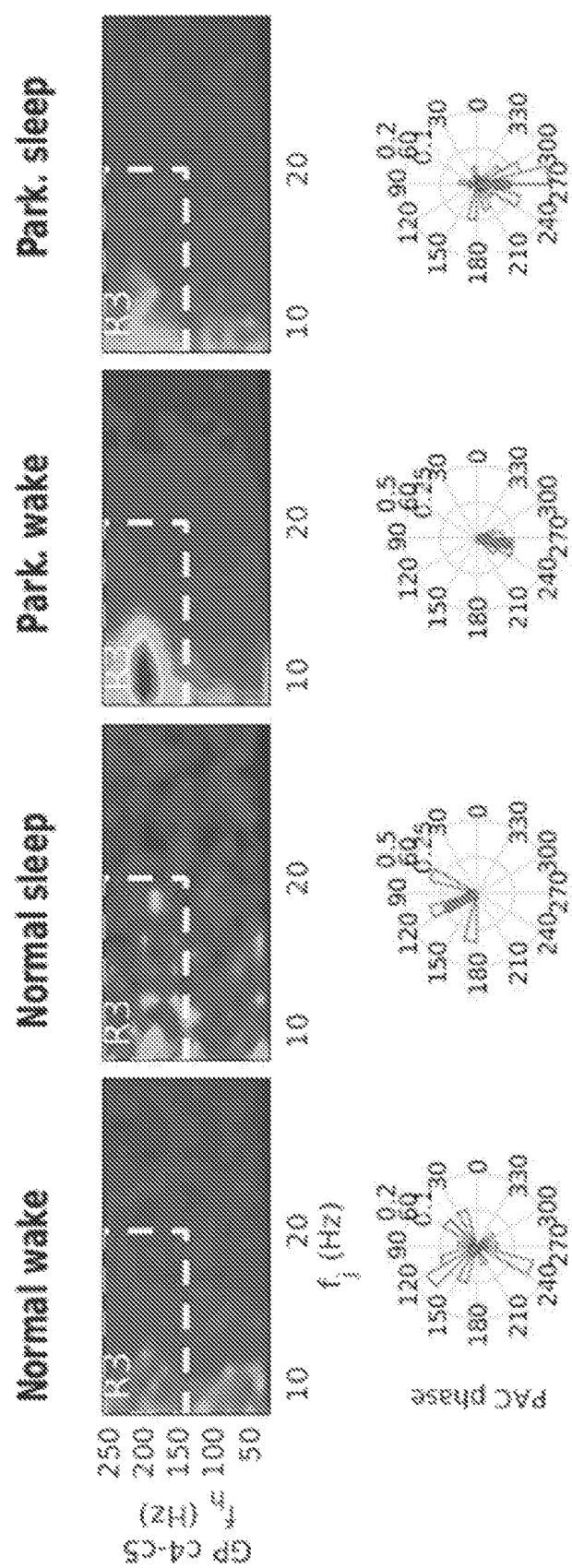
FIG. 7, related to cross frequency correlations, shows that phase amplitude coupling (PAC) emerged in the parkinsonian state in the GP of a NHP subject. This biomarker of disease state was present in the awake condition but reduced during sleep. It is notable that during the early sleep stages reflected here, the parkinsonian symptoms of rigidity were also reduced. This PAC information may also be used to inform sleep staging. The static images represent average activity recorded over many seconds to minutes in each state (awake, sleep). (Analysis can also be performed in more real time as shown in FIG. 8.)

FIG. 7 illustrates the outcome of the sleep detection algorithm using recordings from the STN and how the algorithm compares with sleep assessment using video and cortical recordings. FIG. 7, which is related to cross frequency correlations, shows that phase amplitude coupling (PAC) emerged in the parkinsonian state in the GP of a NHP subject. This biomarker of disease state was present in the awake condition but reduced during sleep. It is notable that during the early sleep stages reflected here, the parkinsonian symptoms of rigidity were also reduced. This PAC information may also be used to inform sleep staging. The static images represent average activity recorded over many seconds to minutes in each state (awake, sleep). Spectral analysis can also be performed in more real time as shown in FIG. 8.

Figure 8:
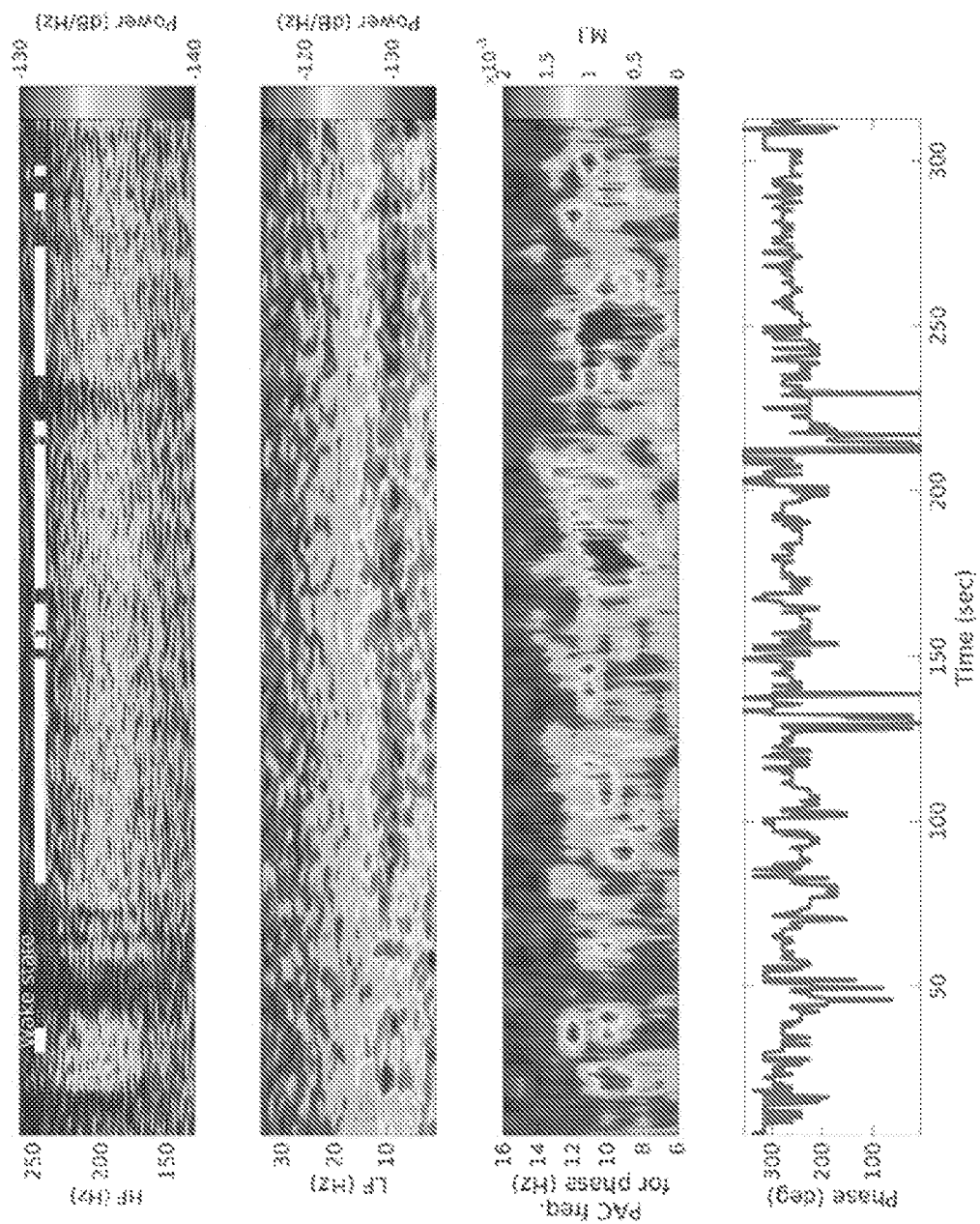
FIG. 8 illustrates, via a spectrogram and a time-comodulogram, how the power and PAC, measured from the GPe of a NHP subject in the parkinsonian condition, evolved over periods in the wake and sleep states.

FIG. 8 illustrates, via a spectrogram and a time-comodulogram, how the power and PAC, measured from the GPe of a NHP subject in the parkinsonian condition, evolved over periods in the wake and sleep states. During periods in the wake state specifically, the spectrogram shows persistent elevated power of low- and high-frequency oscillations associated with the parkinsonian condition. During the sleep state particularly, the power of high-frequency activity (160 to 240 Hz), associated with the parkinsonian condition and PAC, decreased as evidenced by the spectrogram (high-frequency). The sleep state also correlated with a consistent decrease in the M.I. values as observed in the time-comodulogram. When the M.I. was small, the PAC preferred phase fluctuated dramatically.

Figure 9:
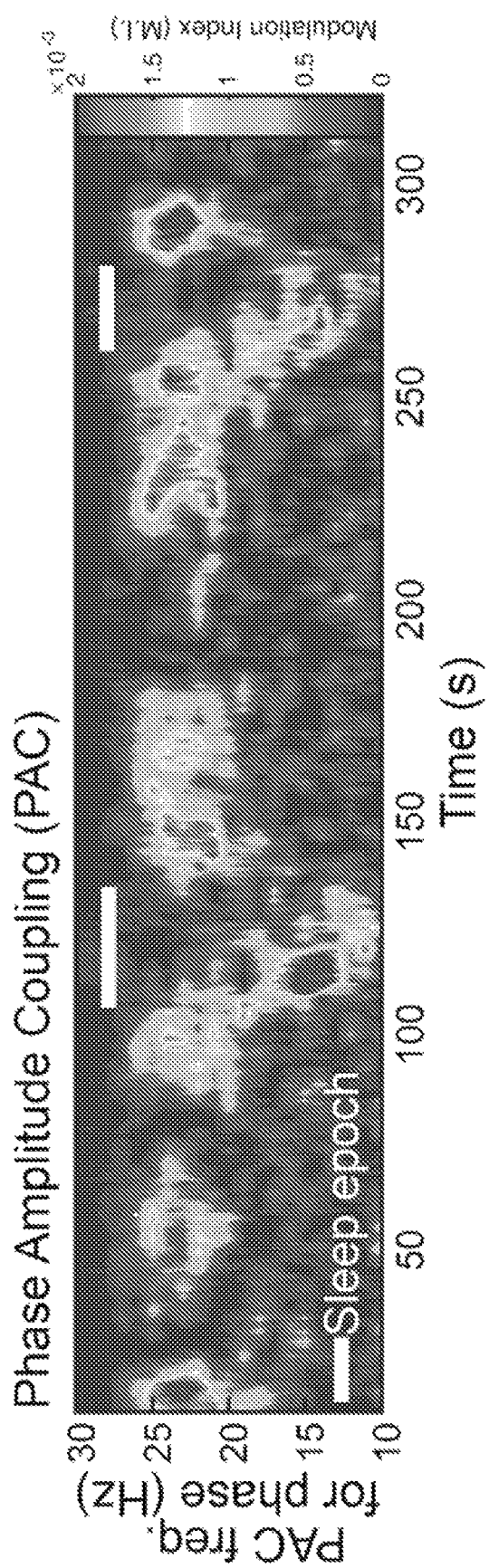
FIG. 9 shows phase amplitude coupling (PAC) is altered in PD, and that PAC measures can provide information about the sleep state (M1 recordings shown).

FIG. 9 shows phase amplitude coupling (PAC) is altered in PD, and that PAC measures can provide information about the sleep state (M1 recordings shown).

In exemplary versions, algorithms and methods may be applied to preexisting implanted or prospective patients with DBS systems to treat PD, essential tremor, dystonia, epilepsy, pain, etc. The algorithms may be uploaded into the firmware with systems capable of brain sensing and delivery of stimulation. Therapy may be applied to de-novo patients with sleep disorders (i.e. insomnia, REM sleep disorder behavior, circadian disorders, restless leg syndrome, etc.) alone or co-morbid with other conditions.

The sensing algorithms may be used to detect and monitor traditional sleep stage waves and correlate with clinical, physiological (i.e. polysomnography) or other objective measures of patient behavior to help give clinicians a diagnosis or monitor progress of conventional therapies. This may also combine with therapeutic algorithms and stimulations to perform closed loop/on demand stimulation to specifically modulate brain circuits to improve brain waves in particular circuits or to improve externally monitored sleep/quality of life.

Stimulation parameters may match, appose, or otherwise be in some mathematical relationship with the brain wave frequencies detected or may be patient specific (determined with trialing, for example). Stimulation parameters may also be varying and/or vary with the various sleep stages and wave patterns throughout a sleep session. Stimulation may simply be a constant (frequency, amplitude, pulse width, wave shape) chronic setting used only during specific sleep cycle time or throughout the day to maintain the optimal sleep circuit tone to promote healthy sleep behavior. Algorithms may also learn and evolve based on patient, clinician, or sensor inputs.

In prospective or existing implants with such capabilities, methods may involve a session of externalization of the DBS lead(s) to perform sensing/recording and stimulation to calibrate/tailor the algorithm to the patient's specific need; brain recordings or observed/recorded behavior may be used in combination with other sensors. The DBS system may comprise the traditional embodiment where a deep brain implanted lead is connected to a subcutaneous extension (or directly connected), which connects to an implanted pulse generator someplace in the body.

Other embodiments may be leadless or extension-less, whereby a minimally-invasive miniature pulse generator with surface electrodes is implanted and fixated (using, e.g., device body anchors) into a deep brain or other brain target to perform sensing and stimulation that improves sleep symptoms. The device may have a primary or rechargeable battery/power supply or be inductively powered by external energies (such as radio frequency (RF), WiFi, microwave, ultrasound, bioenergy, etc.), and may communicate wirelessly and with high fidelity with external control devices and sensors.

It is noted that the site for sensing and stimulation may be the same, or they may be different sites in the brain (or other CNS or PNS targets). For example, sleep stages may be detected at the cortical level and modulation therapy may be delivered via thalamic or other basal ganglia targets. Similarly, sleep stages may be detected in thalamus/STN/GP and therapy may be delivered via modulation of the trigeminal or vagal nerves.

A minimally invasive implant may be a traditional DBS implant procedure or may involve a full asleep/anesthetized procedure with direct MRI (traditional or high field) targeting prediction. The device may be delivered through a minimal (3 mm) twist drill cranial hole or extra-cranially via vasculature or CSF channels using robotics or traditional stereotactic methods.

Therapies provided may be multimodal, in which the original indication is a sleep disorder, and a subsequent comorbid condition arises (e.g., Parkinson's, etc.), or vice versa, and the system can adapt to treat the new conditions (which need not be sleep-related) as well. Additional embodiments of evaluating and modulating sleep using the DBS system 10 are described below.

Sleep Evaluation System with DBS

In certain embodiments, device and software modules may be implemented using the on-board processor of an IPG 12 associated with a DBS system 10 to score sleep stages using an electrode of a DBS lead (e.g. such as electrode selected from the first set of electrodes 32 or the second set of electrodes 36 on IPG 12, see FIG. 2) implanted adjacent to one or more subcortical brain structures (see FIG. 1A). The system can classify sleep stages 'on-line' using the IPG on-board processor or 'off-line' by transferring the sleep data from the IPG to a remote computer, for example wirelessly. In the on-line/on-board mode, signal processing algorithms are executed in the IPG 12 to identify and classify in real-time the sleep stage and temporal features of sleep signals (e.g. K-complexes, spindles) as well as spectral features (e.g. power in different frequency bands). In the off-line mode, the DBS device stores in non-volatile memory (e.g. flash) the monopolar or differential potentials (or a down-sampled version of these potentials) from the DBS lead. The recordings may then be transferred to a host computer, a cloud service, or other remote computing device for off-line staging of sleep. In various embodiments, the off-line mode may be used with IPG devices having low-computational capabilities that are unable to perform sleep staging or to minimize battery consumption associated with onboard processing.

The sleep status of the subject can be assessed using monopolar and/or bipolar recordings from one or more subcortical structures (e.g. the subthalamic nucleus (STN), the globus pallidus internal (GPI) segment, the globus pallidus external (GPe) segment, or the thalamus) and/or other brain areas if applicable (e.g. as identified by cortical surface electrocorticography (ECoG) arrays). In some embodiments, monopolar recordings can be used to accurately sense low-frequency oscillations, whereas in other embodiments bipolar recordings can be used to improve the sensing capabilities at higher frequencies.

Figure 10:
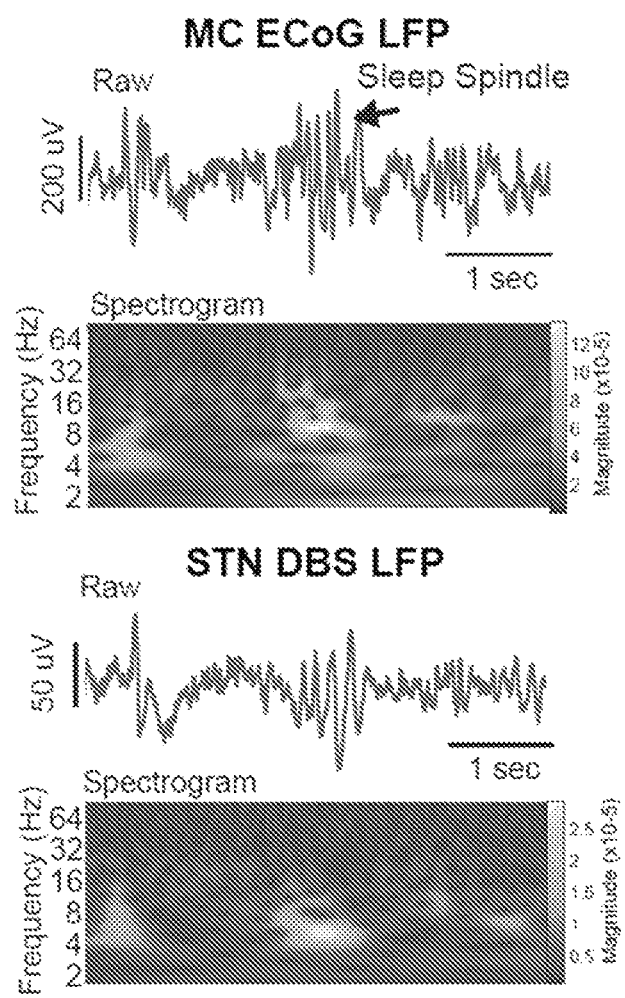
FIG. 10 shows sleep spindles associated with sleep simultaneously recorded in both cortical regions (ECoG on primary motor cortex, "MC ECoG LFP") and in the STN (DBS lead, "STN DBS LFP"). Spindles are detected using wavelet spectrograms that have the time resolution to enable their detection. The maximum power of the spindle in the STN can occur at a lower frequency than for spindles in cortical regions.

Surprisingly, it has been determined that spindles and K complexes, observed via EEG and ECoG recordings and similar to those used for traditional sleep staging studies, are also observed in the subcortical structures of NHPs. This surprising observation, which was made with NHPs, has in turn been used to develop a DBS system that scores the sleep stage of a subject using sleep scoring approaches applied to potentials measured in subcortical structures. Thus in various embodiments, the sleep scoring mode of the DBS system 10 uses automatic detection of one or more of: spindles, K-complexes, and relative power (i.e. power normalized with respect to total power across measured frequencies) in different frequency bands (e.g. delta, theta, alpha, beta) to classify and score the sleep stages. In general, the relative power in frequency bands can be used to determine NREM and REM stages based on the observation that all sleep stages have high delta and theta power, whereas NREM has low beta and gamma power and REM has high beta and gamma power. Spindles are generally detected based on the envelope of oscillations in the 11-16 Hz band (although the specific frequency band to use can be recording site-dependent, for example, STN spindle detection may in some cases require a lower frequency range, as shown in FIG. 10) and time domain feature extraction techniques based on wavelets. The K-complexes are generally detected using the envelope of oscillations in the 0.5-2 Hz band and time domain feature extraction techniques based on wavelets. Software routines for spindle and K-complex detection can be uploaded onto the device firmware to perform detection in the on-line/on-board mode.

In some embodiments, onboard sensors in the IPG such as tri-axial accelerometers or tri-axial gyroscopes (if available) may be used to verify that the subjects are resting and thereby as a secondary metric to validate the sleep states.

In further embodiments, wearable sensors such as accelerometers and gyroscopes may be used to determine motion of the limbs during REM sleep and to provide information (e.g. for use by clinicians or closed-loop DBS algorithms) about REM sleep behavior disorder (RBD) signs (e.g. acting out vivid dreams). Sensors of heart rate and blood pressure may also be used together with the IPG data/algorithms to verify REM sleep stages and to supplement the sleep recordings from the subcortical DBS electrodes. In certain embodiments these sensors may transfer data to the IPG wirelessly.

In still other embodiments, the sleep evaluation algorithm may be personalized to a particular subject and may be optimized with feedback from traditional polysomnography (PSG) recordings, recordings obtained, for example, in a sleep clinic setting or in a residence using home-based mobile devices to collect data and to evaluate the best contacts/contact pairs to use for sensing and classification. A software platform (e.g. software used for IPG programming or another platform) can execute the optimization algorithms (e.g. gradient-based optimization, least squares) to optimize the selection of electrodes that best predict the PSG assessments.

DBS System with Automatic Sleep Mode Control to Minimize Stimulation During Sleep and Maximize Battery Life In some embodiments, particular sleep stages including NREM and REM may be detected and identified based on data indicative of cortical or subcortical activity, for example monopolar and/or differential (bipolar) potentials recorded from DBS leads. Identification of particular sleep stages may then be used to modulate the operation of an implantable device such as the DBS system 10, as discussed further below.

Identification of particular sleep stages may be based at least in part on signal characteristics such as the amplitude of low frequency oscillations in the STN and/or GPi, which are generally higher in all the sleep stages than in the awake state. In various embodiments disclosed herein, the sleep mode algorithms of the DBS system 10 may use real-time measurements of low-frequency power and/or proportions of power in different frequency bands (e.g. delta, theta, alpha, beta, gamma) to identify whether the subject is awake or asleep.

In further embodiments, algorithms such as those used by the IPG 12 to identify spindles and K complexes in real-time may also be used in the sleep mode to verify whether the subject is in an NREM sleep stage (or other sleep stage, such as REM) and to minimize the occurrence of false sleep detections. Accordingly, when a sleep state is detected the DBS system 10 (as guided by the sleep mode algorithm) may automatically reduce therapeutic stimulation (e.g. used for treating a condition other than a sleep disorder) by a desired level (e.g. 80%, a figure that may be configurable by the subject or by a clinician/physician); thus, the DBS system 10 with 'sleep mode' may automatically detect sleep and decrease therapeutic stimulation. When data indicates that the subject is waking up, the sleep mode may be automatically suspended/disabled and the DBS therapeutic settings may be restored to alleviate the symptoms of the subject (e.g. motor symptoms in PD). This automatically detected and managed sleep mode provides more comfort to patients than manually-operated sleep modes in which the patients must manually turn the device on or off (e.g. using an external programmer device) or program the times of activation and deactivation of the electrical stimulation ahead of time. For example, using the automatic sleep mode a subject who wakes up unexpectedly in the middle of the night (e.g. to use the restroom) may have his or her therapeutic settings restored (which in some embodiments may be done gradually so that the therapy is ramped up) to relieve symptoms to enable the subject to get up and move about, without having to use the programmer to manually turn the device on.

Sleep Modulation

In various embodiments, monitoring and detection of sleep stages may be used to modulate the sleep of the subject in a 'sleep enhancement mode.' The sleep enhancement mode may be activated by the subject or a clinician, which may be performed, for example, via the patient/clinician IPG programmers.

A subject's sleep may be modulated/facilitated by actively amplifying low-frequency (e.g. slow-wave, delta, theta, alpha) neural activity and thereby promoting or enhancing natural rhythms that are associated with various sleep stages. By promoting natural rhythms for periods of time that are comparable to those observed in healthy subjects, embodiments of the DBS system 10 disclosed herein may regularize sleep in DBS subjects who want to improve their sleep or in other subjects (who may not be in need of DBS therapy) who have been diagnosed with a sleep disorder.

Thus, a novel feature of embodiments of the DBS system 10 disclosed herein is the ability to amplify sleep-related rhythms in cortical regions of the brain of the subject based on cortical potentials evoked by electrical stimulation in subcortical structures. Amplification of cortical and thalamic potentials at low-frequency via sub cortical stimulation promotes the synchronization of thalamocortical circuits and the disconnection between peripheral stimuli and cortical regions, ultimately facilitating non-REM sleep.

In various embodiments, a particular electrode is selected to be a stimulation electrode based on the particular electrode producing the largest evoked potentials in cortical regions. The particular electrode that is selected is used to amplify low-frequency oscillations (0.1-30 Hz) in the cortex, as it is the most capable of modulating cortical activity (i.e. has the highest 'controllability'). Controllability measurements (which are used to select the sleep modulation electrode), such as the peak to peak amplitude, can be calculated online by the IPG or offline by a host computer, cloud service, or other remote computing device. In various embodiments, the cortical potentials may be measured via non-invasive EEG recordings or intra-cranial ECoG (if available).

In certain embodiments, sensors may also be placed in the peripheral nervous system (e.g. electromyography (EMG) electrodes, spinal cord leads, peripheral nerve sensors) to be used instead of, or in addition to, cortical output and to measure DBS cortical controllability for electrode selection. In various embodiments, the electrode(s) for stimulation may be selected during an IPG programming session and may not necessarily be those used for therapeutic purposes (e.g. to alleviate motor symptoms). Therefore, embodiments of sleep modulation and DBS therapy (e.g. motor relief in Parkinson's disease) may be performed using the same or different electrical stimulation sources and DBS electrodes.

If the DBS electrode(s) used for treatment of primary symptom(s) (e.g. motor symptoms in PD) are different from those selected for sleep modulation, and if the IPG has two independent current sources, the DBS system 10 in certain embodiments may simultaneously deliver DBS for both sleep and the primary symptom. In other embodiments, if the same electrode(s) and/or current source(s) need to be used for both sleep modulation and for treatment of the primary symptom(s), the system can deliver the sleep-specific stimulation pattern superimposed on the primary DBS treatment stimulation pattern, which may be adjusted as necessary to maintain balance of electrical charge delivered.

In some embodiments, neuromodulation of the target brain structures that are part of the sleep circuitry may be performed using other techniques instead of (or in addition to) electrical stimulation via implanted electrodes. For example, neuromodulation may be performed using techniques such as transcranial focused ultrasound, transcranial magnetic stimulation (TMS), transcranial direct current stimulation (tDCS), and/or transcranial alternating current stimulation (TACS). In further embodiments, the DBS system 10 may be integrated with a drug delivery system which may be used instead of (or in addition to) electrical or other stimulation described above. In this embodiment, drug therapy (e.g. levodopa) may be adjusted based on sensing by the DBS device 10; a drug may be delivered to the subject, for example, by interfacing with a drug delivery system (e.g. patch/pump systems such as Duopa or NeuroDerm). In certain embodiments, various sleep disorder-related medications may also be administered to the subject based on sleep sensing/evaluation. For example, medications may be delivered to individuals with narcolepsy to wake them up during a sleep attack or to prevent an attack, where the medication may be administered using on-command signals sent from the DBS system 10 based on the sleep sensing/evaluation algorithms.

Open Loop Mode

In various embodiments, the control of cortical evoked responses may be achieved via open-loop and/or closed-loop modes. In the open-loop mode, the system does not take into account neural oscillatory activity already present in the subcortical or cortical structures. Instead, the system delivers patterned stimulation (e.g. low-frequency bursts or amplitude-modulated stimulation) to promote amplification of low-frequency oscillations in the thalamocortical networks that are associated with sleep. This may continue throughout the sleeping period, as determined by the scheduler (defined below) or by the user/subject. In certain embodiments, stimulation may include a charge-balanced pulse train whose current amplitude and/or frequency is modulated such that maximal energy is delivered at a defined frequency Fc (e.g. square, triangular, sinusoidal envelopes), with the rationale that brain signals will become entrained to the stimulation. Fc is the frequency at which amplification of thalamocortical oscillations is desired. Exemplars of stimulation signals may include: a Fc Hz pulse train; a pulse train with high carrier frequency (e.g. traditional 130 Hz) that is amplitude modulated by a Fc Hz sinusoidal envelope; a pulse train with high carrier frequency (e.g. traditional 130 Hz) that is frequency modulated by a Fc Hz sinusoidal signal; or burst stimulation with N pulses and inter-burst frequency Fc.

Closed Loop Mode

In particular embodiments, at least two modes of closed-loop sleep neuromodulation are possible: (1) DBS feedback mode and (2) cortical or external sensor feedback mode (see schematic diagrams of one embodiment of the system shown in FIGS. 11 and 12). In the DBS feedback mode (e.g. as discussed above), feedback may be obtained from the same DBS lead that has been implanted for therapeutic purposes (e.g. to treat sleep disorders, Parkinson's disease, essential tremor, dystonia, etc.). The rationale behind using the DBS leads for sensing is that subcortical structures typically targeted for DBS therapies (e.g. STN, GP, thalamus) are functionally connected and synchronized with thalamic and cortical regions (e.g. motor cortex, supplementary motor area) and other brain areas involved with sleep (e.g. connections to brainstem nuclei involved with sleep such as the peduncolopontine nucleus). In the closed-loop with cortical feedback mode, on the other hand, feedback is obtained from recordings from ECoG electrodes implanted in the cortex. In particular embodiments of the closed-loop with cortical feedback mode, feedback may be obtained from EEG electrodes placed non-invasively on the scalp or from any external sensor capable of sensing cortical output (e.g. spinal cord leads or EMG electrodes) instead of from ECoG electrodes.

In either mode (i.e. DBS or cortical feedback), the feedback signals may be filtered in the frequency band where amplification of oscillations is intended; various filtering approaches, for example a Butterworth filter, may be used.

In various embodiments, electrical stimulation artifacts produced by current conductance through brain tissue, but not by neuronal activity, may be removed from the feedback signal using a filter such as an infinite impulse response (IIR) filter or a finite impulse response (FIR) filter. The filter parameters may be calculated during a DBS programming session, and these calculations may be performed using system identification algorithms (e.g. output error, instrumental variable, subspace identification, ARX, ARMAX). A schematic of the artifact removal system is presented in FIG. 12. Time-varying, online system identification techniques (e.g. recursive least squares estimator, recursive polynomial estimator, Kalman Filter, or Gradient optimization) may also run on the IPG onboard computer to estimate the filter parameters online. This online identification may be useful when the artifact shape and/or size vary over time.

Figure 11:
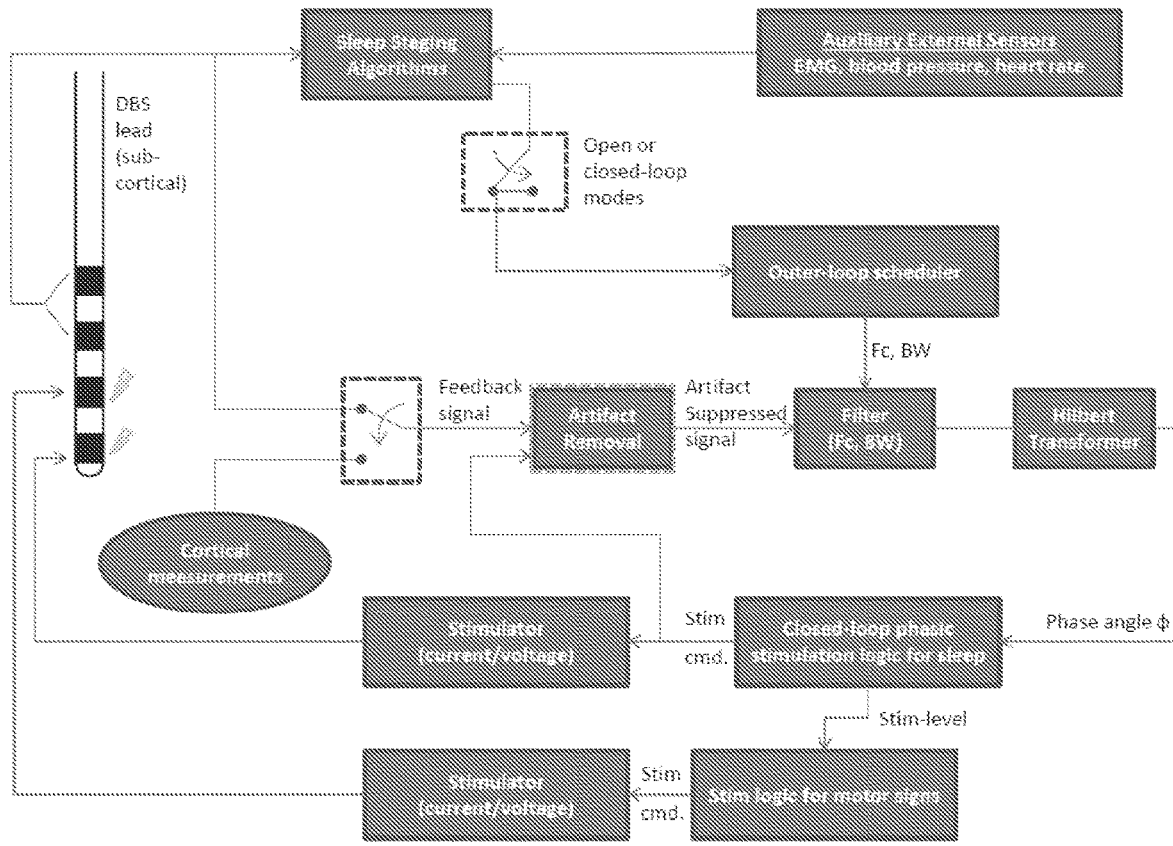
FIG. 11 shows a schematic diagram of an embodiment of a sleep modulation system.
Figure 12:
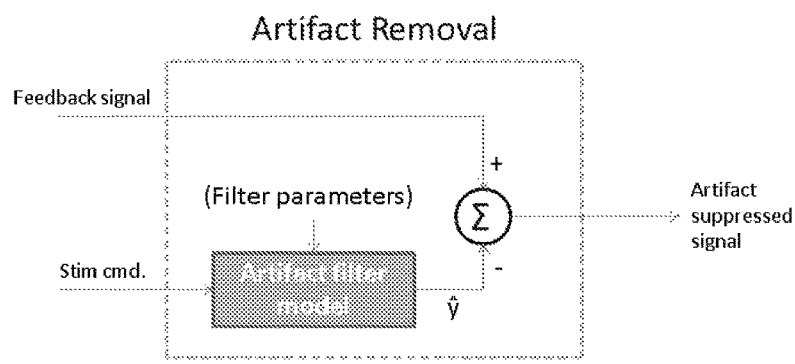
FIG. 12 shows a schematic of an embodiment of an artifact removal system shown in FIG. 11.

FIG. 12 shows a schematic of an embodiment of an artifact removal system shown as part of the system of FIG. 11. The filter parameters may be obtained via online (in the IPG) or offline (e.g. in a host computer or an IPG programmer) system identification of the artifacts (e.g. using any system identification method). The artifacts and evoked potentials may be differentiated by using data in which both anodal and cathodal stimulation are delivered. The artifacts from cathodal and anodal stimulation cancel out, whereas the evoked responses do not.

In embodiments of the closed-loop mode, the stimulator may deliver a train of N pulses with intra-burst frequency Fi that is phased-locked to the measured oscillations in the target frequency band with center frequency Fc, where the number of pulses (N) and intra-burst frequency (Fi) may be configurable parameters. Additionally, the amplitude of the stimulation pulses can be configured to increase and decrease with a rate of change equal to Rp. In other words, the stimulation pulse amplitude follows a trapezoidal profile with slopes equal to Rp. A smooth transition between pulse amplitudes instead of an abrupt transition can help reduce side effects (e.g. paresthesias in PD patients implanted with DBS in the STN).

The phase of the feedback signals (e.g. band-pass filtered in the frequency band with center frequency Fc) used to deliver phasic stimulation may be calculated in real-time using a Hilbert Transformer (e.g. FIR filter) or other suitable phase estimation technique (e.g. phase-locked loop, PLL). The embedded IPG computer may use the phase estimation to trigger the stimulation bursts with configured parameters N and Fi at the phase angle associated with maximum amplification of the oscillations in the feedback signal. The optimal phase angle may be automatically determined by the onboard IPG processor or by the host computer connected wirelessly with the IPG via a search over angles between 0 and 360 degrees. Optimization algorithms such as the Gradient Descent or Bisection Algorithm can also be used to efficiently find an optimal phase angle at which stimulation maximizes the amplitude of the target oscillations.

The optimal phase angle at which stimulation minimizes the amplitude of target oscillations may also be determined and used to cause destructive interference and reduce oscillations in a particular frequency band. Therefore, in various embodiments the method described herein may be extended to suppress neural oscillations across selected frequency bands associated with neurological and psychiatric disorders (e.g. epilepsy, dystonia, Parkinson's disease, depression, obsessive compulsive disorder).

Sleep Scheduler

In certain embodiments of the sleep modulation algorithm, a 'sleep scheduler' may be provided which permits a subject or clinician to design a desired sleep pattern, or 'sleep architecture' (i.e. a healthy architecture target). The targeted frequency band with center frequency Fc may be controlled by an outer-loop scheduler that tracks the desired sleep architecture (note that Fc is used in both the open-loop and closed-loop modes described above and so the sleep scheduler is applicable to either mode).

The target sleep architecture may be defined in the IPG programming session by selecting the desired time windows for each stage (N1, N2, N3, REM) in each cycle of sleep (e.g. two to six cycles total). The time windows may be configured differently in each cycle; for example, longer periods of REM sleep may be desired in the third and fourth cycles to mimic the sleep patterns of healthy subjects. Thus the target frequency band and its center frequency Fc may vary slowly over time, starting in the alpha band and moving to the theta and delta bands as time progresses. The target frequency may be rapidly increased following the delta band to serve as a reference frequency for REM sleep. The rate of change to increase Fc may also be configured. When the target frequency Fc reaches the beta band, the scheduler may turn off the phasic stimulation aimed to entrain thalamocortical low-frequency oscillations.

In various embodiments, the sleep scheduler may also enable beta-band (~10-30 Hz) phasic stimulation to promote synchrony in the beta band and thereby reduce body movements associated with REM sleep behavior disorder (RBD). The rationale behind this idea is that beta band stimulation has been reported to increase akinesia in Parkinson's disease patients. Phasic stimulation may be more effective in amplifying beta oscillations than open-loop stimulation with frequency in the beta band. Although akinesia may not be desired during waking hours, in patients with RBD it may be desirable to attenuate excessive movements that can occur during REM sleep stage. After the REM target period completes, the scheduler may decrease the target frequency towards the delta band to cycle through N1, N2, and N3 stages again. The subject or their clinician may decide to program more than two incursions into the N3 stage. In sum, the target frequency of the sleep architecture follows and mimics the dominant oscillatory frequencies observed in healthy sleep architectures and serves as a reference for the inner-loop phasic stimulation algorithm to amplify neural activity in specific frequency bands.

Figure 13:
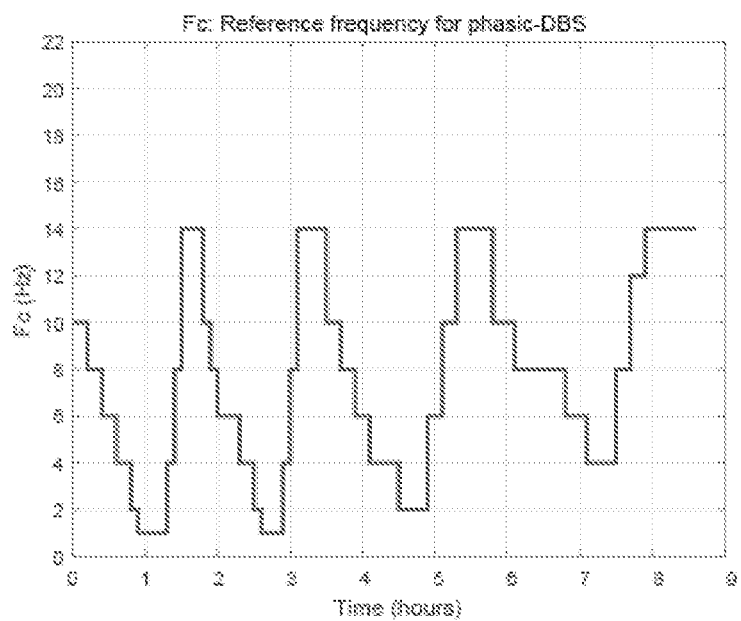
FIG. 13 shows a schematic of a reference frequency generated by outer-loop scheduler.

The outer-loop controller that schedules the target frequency band for amplification may operate in an open-loop mode or a closed-loop mode. In the open loop mode, the target frequency band and its center frequency may be changed according to a predetermined program without taking into account the actual sleep stage of the subject. The changes in the target frequency may occur in a stepwise (FIG. 13) or continuous manner. FIG. 13 shows a schematic of a reference frequency generated by an outer-loop scheduler, where Fc is the center frequency for the frequency band in which phasic closed-loop stimulation may be delivered to amplify oscillations. The reference profiles may be configured during the programming sessions.

In the closed-loop mode, the scheduler may wait until the actual dominant oscillatory power is at the target frequency band for the desired duration before moving to the next target frequency band. In the closed loop mode, the changes in target frequency band occur in steps (discrete transitions). Identification of time domain signal features (e.g. spindles, K-complexes) and spectral characteristics of the neural signals may help the closed-loop scheduler to confirm whether the subject is in a REM or NREM sleep stage.

In some embodiments, sensors measuring EMG, heart rate, and/or blood pressure can be used to improve the classification between REM and non-REM stages, based on the observation that REM sleep is generally characterized by higher heart rate and blood pressure than non-REM stages and by low-amplitude EMG readings as compared to non-REM and awake stages. A smart-watch with EMG and blood pressure sensors connected to the IPG (e.g. wirelessly using Bluetooth, ZigBee, or other suitable communication technology) may be used to improve the aforementioned sleep classification.

In various embodiments, sleep modulation may be provided for particular sleep disorders, including: insomnia/excessive daytime sleepiness; sleep attacks/narcolepsy; and REM sleep behavior disorder:

Insomnia/Excessive Daytime Sleepiness

It is anticipated that use of embodiments of the DBS system 10 to regularize various sleep stages may enhance sleep metrics such as sleep efficiency, REM start time, and number of sleep cycles (i.e. the number of times REM stage sleep occurs), which may be favorable for subjects with insomnia. It is anticipated that improved sleep efficiency will improve (i.e. reduce) daytime sleepiness.

Sleep Attacks/Narcolepsy

Sleep attacks (i.e. a sudden involuntary episode of sleep) and narcolepsy are often considered to occur as a side effect of medications. In various embodiments, sleep detection processing may be used during waking hours to alert the patient of sleep-like activity and to send a signal to an external device (e.g. an alarm on a patient programmer or a smart watch) to the subject to wake up and take appropriate medication (if applicable), or to trigger a different set of stimulation parameters that may interfere with the subject's transition into sleep.

REM Sleep Behavior Disorder

As discussed above, the sleep scheduler may also enable beta-band (~10-30 Hz) phasic stimulation aimed at promoting synchrony in the beta band and thereby reduce body movements associated with REM sleep behavior disorder (RBD).

Example

Figure 14:
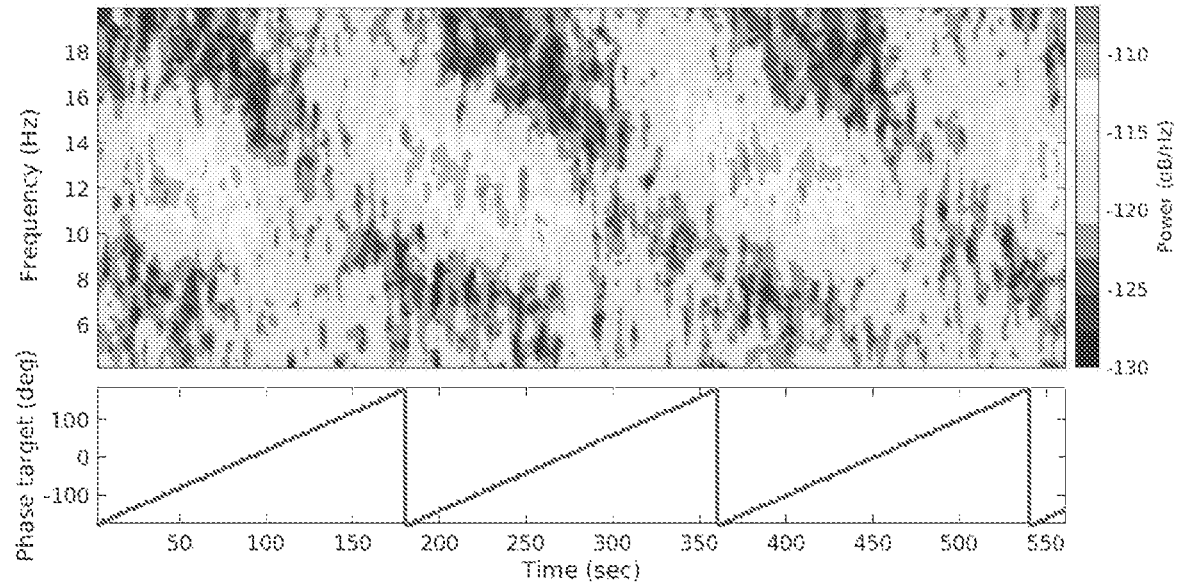
FIG. 14 shows a spectrogram showing the modulation of power of STN local field potentials (LFPs, differential potentials) depending upon the phase of phasic stimulation of the STN of a non-human primate.

Data collected in a non-human primate (NHP) during phasic stimulation (as described above) shows that it is possible to modulate low-frequency neural activity in the STN using STN recordings. The upper panel of FIG. 14 is a spectrogram which shows the power of STN local field potentials (LFPs, differential potentials) during phasic stimulation of the STN of a non-human primate, where the STN LFPs were used for feedback. Stimulation was delivered at different phase angles of the STN oscillations, as shown in the lower panel of FIG. 14. The target frequency was Fc=12 Hz, the bandwidth BW=4 Hz, the intra-burst frequency Fi=165 Hz, and the number of pulses for the burst N=4. The oscillatory power at 12 Hz was amplified when the stimulation was delivered at specific phase angles (~90 to 0 degrees) of the neural oscillations. The power was suppressed at approx. 90 degrees. Stimulation evoked potentials phase-locked to the neural oscillations are the primary cause of changes in power observed in the spectrogram. These data show that phasic stimulation is capable of modulating neural activity in subcortical structures at low frequency. LFPs were recorded and stimulation was delivered using a DBS lead (NuMed) which is a scaled-down version of human DBS leads. The algorithms in this experiment were executed in a real-time control computer with a sampling frequency of 25 KHz. LFPs were recorded and transmitted to the real-time control computer using a TDT Neurophysiological recording system (25 KHz sampling rate). The TDT system was also used to deliver electrical stimulation to the STN (current stimulation).

The present invention has been described in terms of one or more preferred embodiments, and it should be appreciated that many equivalents, alternatives, variations, and modifications, aside from those expressly stated, are possible and within the scope of the invention.

What is claimed is:

1. A method for controlling a sleep pattern of a subject, comprising the steps of:
   receiving electrical data obtained from a deep brain stimulator (DBS) implanted in a subcortical structure including a globus pallidus of a brain of the subject;
   determining that the subject is in an awake state based on analyzing the electrical data from the subcortical structure based on first phase amplitude coupling (PAC) data from the globus pallidus;
   analyzing the electrical data from the DBS implanted in the subcortical structure to identify second PAC data, the second PAC data being reduced compared to the first PAC data from the awake state;
   determining that the subject is in an NREM sleep stage based on identifying at least one of a K complex or a spindle in the second PAC data and; and
   stimulating, based on determining that the subject is in the NREM sleep stage, the subcortical structure of the brain of the subject by applying a patterned stimulation to the subcortical structure with a stimulation frequency of 10 Hz to at least one of induce sleep or awaken the subject.

2. The method of claim 1, wherein the patterned stimulation includes a charge balanced pulse train comprising a maximal energy delivered at a center frequency Fc to amplify oscillations with center frequency Fc.

3. The method of claim 2, further comprising identifying a phase angle of the electrical data associated with a maximum amplification of oscillations with center frequency Fc, and
   stimulating the subcortical structure of the brain of the subject at the identified phase angle using at least one electrode of the DBS.

4. The method of claim 1, wherein the globus pallidus includes at least one of a globus pallidus internal (GPI) segment, a globus pallidus external (GPe) segment, and the subcortical structure further includes one of: a subthalamic nucleus (STN) or a thalamus.

5. The method of claim 1, wherein the electrical data comprises a plurality of frequency bands, and wherein determining that the subject is in the NREM sleep stage further comprises:
   determining that the subject is in the NREM sleep stage based on calculating a relative power associated with each of the plurality of frequency bands.

6. The method of claim 1, wherein, when the patterned stimulation has been applied to induce sleep, the method further comprises:
   adjusting control of the DBS to reduce the patterned stimulation based on determining that the subject is in the NREM sleep stage.

7. The method of claim 1, further comprising:
   stopping application of the patterned stimulation,
   receiving further electrical data obtained from the subcortical structure of the brain of the subject,
   determining that the subject is no longer in the NREM sleep stage based on analyzing the further electrical data, and
   resuming the patterned stimulation of the DBS based on determining that the subject is no longer in the NREM sleep stage.

8. The method of claim 1, wherein determining that the subject is in the NREM sleep stage based on analyzing the electrical data further comprises:
   determining that the subject is asleep during a preprogrammed waking period, and
   adjusting control of the DBS based on determining that the subject is in the NREM sleep stage by transmitting a signal from the DBS to alert the subject to wake up.

9. The method of claim 1, wherein determining that the subject is in the NREM sleep stage includes determining a power of activity of the electrical data in a frequency range of 160 to 240 Hz.

10. The method of claim 1, wherein the stimulation frequency of 10 Hz reduces body movements of the subject.

11. The method of claim 1, further comprising recording the electrical data using the DBS.

12. The method of claim 1, wherein stimulating the subcortical structure is performed at a different site than a site for receiving the electrical data from the subcortical structure.

13. The method of claim 1, wherein stimulating the subcortical structure of the brain of the subject includes enhancing sleep metrics including at least one of sleep efficiency, REM start time, number of sleep cycles, or a number of times a REM stage sleep occurs.

14. The method of claim 1, further comprising:
   determining that the subject is asleep during a preprogrammed waking period, and
   alerting, based on determining that the subject is asleep during the preprogrammed waking period, the patient by performing at least one of:
      sending a signal to an external device for the subject to wake up, or
      triggering a different set of stimulation parameters to interfere with the subject's transition into sleep.

15. The method of claim 14, wherein the external device includes at least one of a patient programmer or a smart watch.

16. A system for controlling a sleep pattern of a subject, comprising a controller including a processor and instructions that, when executed by the processor, configure the system to:
   receive electrical data obtained from a deep brain stimulator (DBS) implanted in a subcortical structure including a globus pallidus of a brain of the subject;

determine that the subject is in an awake state based on analyzing the electrical data from the subcortical structure based on first phase amplitude coupling (PAC) data from the globus pallidus;

analyze the electrical data from the DBS implanted in the subcortical structure to identify second PAC data,
the second PAC data being reduced compared to the first PAC data from the awake state;

determine that the subject is in an NREM sleep stage based on identifying at least one of a K complex or a spindle in the second PAC data and; and stimulate the subcortical structure of the brain of the subject by applying a patterned stimulation to the subcortical structure with a stimulation frequency of 10 Hz to at least one of induce sleep or awaken the subject based on determining that the subject is in the NREM sleep stage.

17. The system of claim 16, wherein the patterned stimulation includes a charge balanced pulse train comprising a maximal energy delivered at a center frequency Fc to amplify oscillations with center frequency Fc.

18. The system of claim 17, wherein the processor is further configured to identify a phase angle of the electrical data associated with a maximum amplification of oscillations with center frequency Fc, and
stimulate the subcortical structure of the brain of the subject at the identified phase angle using at least one electrode of the DBS.

19. The system of claim 16, wherein the globus pallidus includes at least one of a globus pallidus internal (GPI) segment, a globus pallidus external (GPe) segment, and the subcortical structure further includes one of: a subthalamic nucleus (STN) or a thalamus.

20. The system of claim 16, wherein the electrical data comprises a plurality of frequency bands, and wherein the processor is further configured to determine that the subject is in the NREM sleep stage based on calculating a relative power associated with each of the plurality of frequency bands.

21. The system of claim 16, wherein, when the patterned stimulation has been applied to induce sleep, the processor is further configured to:
adjust control of the DBS to reduce the patterned stimulation based on determining that the subject is in the NREM sleep stage.

22. The system of claim 16, wherein the processor is further configured to:
stop application of the patterned stimulation,
receive further electrical data obtained from the subcortical structure of the brain of the subject,
determine that the subject is no longer in the NREM sleep stage based on analyzing the further electrical data, and
resume the patterned stimulation of the DBS based on determining that the subject is no longer in the NREM sleep stage.

23. The system of claim 16, wherein the processor is further configured to determine that the subject is in the NREM sleep stage based on analyzing the electrical data by determining that the subject is asleep during a preprogrammed waking period, and wherein the processor is further configured to adjust control of the DBS based on determining that the subject is in the NREM sleep stage by transmitting a signal from the DBS to alert the subject to wake up.

24. The system of claim 16, wherein the processor is further configured to determine that the subject is in the NREM sleep stage by determining a power of activity of the electrical data in a frequency range of 160 to 240 Hz.

25. The system of claim 16, wherein the stimulation frequency of 10 Hz reduces body movements of the subject.

26. The system of claim 16, wherein the processor of the controller is further configured to record the electrical data.

27. The system of claim 16, wherein the processor is further configured to stimulate the subcortical structure at a different site than a site for receiving the electrical data from the subcortical structure.

28. The system of claim 16, wherein the processor is further configured to stimulate the subcortical structure of the brain of the subject to enhance sleep metrics including at least one of sleep efficiency, REM start time, number of sleep cycles, or a number of times a REM stage sleep occurs.

29. The system of claim 16, wherein the processor is further configured to:
determine that the subject is asleep during a preprogrammed waking period, and
alert, based on determining that the subject is asleep during the preprogrammed waking period, the patient by performing at least one of:
sending a signal to an external device for the subject to wake up, or to trigger
triggering a different set of stimulation parameters to interfere with the subject's transition into sleep.

30. The system of claim 29, wherein the external device includes at least one of a patient programmer or a smart watch.

31. A method for controlling a sleep pattern of a subject, comprising the steps of:
receiving electrical data from a subcortical region of a brain of the subject obtained from a sensor;
determining that the subject is in an awake state based on analyzing the electrical data based on first phase amplitude coupling (PAC) data from the subcortical region of the brain of the subject;
analyzing the electrical data to identify second PAC data, the second PAC data being reduced compared to the first PAC data from the awake state;
determining that the subject is in an NREM sleep stage based on identifying at least one of a K complex or a spindle in the second PAC data; and
stimulating the subcortical region of the brain of the subject by applying a therapeutic stimulation with a stimulation frequency of 10 Hz to at least one of induce sleep or awaken the subject based on determining that the subject is in the NREM sleep stage.

32. The method of claim 31, wherein the sensor is at least one of an EEG electrode or ECOG array, and
wherein receiving electrical data of the subcortical region of the brain of the subject includes data obtained from the at least one EEG electrode or ECOG array.

* * * * *

UNITED STATES PATENT AND TRADEMARK OFFICE
CERTIFICATE OF CORRECTION

| | |
|---|---|
| PATENT NO. | : 11,318,311 B2 |
| APPLICATION NO. | : 17/002136 |
| DATED | : May 3, 2022 |
| INVENTOR(S) | : Molnar et al. |

It is certified that error appears in the above-identified patent and that said Letters Patent is hereby corrected as shown below:

In the Claims

Column 24, Claim 29, Line 30, "or to trigger" should be --or--.

Signed and Sealed this
Twenty-eighth Day of June, 2022

Katherine Kelly Vidal
*Director of the United States Patent and Trademark Office*